United States Patent
Zanni et al.

(10) Patent No.: US 7,771,938 B2
(45) Date of Patent: Aug. 10, 2010

(54) NONLINEAR SPECTROSCOPIC METHODS FOR IDENTIFYING AND CHARACTERIZING MOLECULAR INTERACTIONS

(75) Inventors: Martin T. Zanni, Madison, WI (US); John C. Wright, Oregon, WI (US); Eric C. Fulmer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 433 days.

(21) Appl. No.: 11/228,042

(22) Filed: Sep. 15, 2005

(65) Prior Publication Data

US 2006/0063188 A1     Mar. 23, 2006

Related U.S. Application Data

(60) Provisional application No. 60/611,408, filed on Sep. 20, 2004.

(51) Int. Cl.
    *C12Q 1/68*     (2006.01)
    *G01N 33/53*   (2006.01)
    *A61K 38/00*   (2006.01)
    *C07K 1/00*     (2006.01)
    *C07H 21/02*   (2006.01)

(52) U.S. Cl. .................. 435/6; 435/7.1; 530/300; 530/350; 536/23.1

(58) Field of Classification Search ............... 435/6, 435/7.1, 91.1, 183; 436/94, 501; 536/23.1, 536/24.3; 530/300, 350
See application file for complete search history.

(56) References Cited

U.S. PATENT DOCUMENTS

| | | | |
|---|---|---|---|
| 4,759,613 A | 7/1988 | Fox | |
| 5,526,171 A | 6/1996 | Warren | |
| 5,600,444 A | 2/1997 | Tong | |
| 5,891,643 A | 4/1999 | Fesik et al. | |
| 5,989,827 A | 11/1999 | Fesik et al. | |
| 6,141,094 A | 10/2000 | Tong | |
| 6,621,613 B2 | 9/2003 | Silberberg et al. | |
| 6,677,160 B1 | 1/2004 | Stockman et al. | |
| 6,764,858 B2 | 7/2004 | Stockman | |
| 7,064,844 B2 | 6/2006 | Budach et al. | |
| 2003/0099264 A1 | 5/2003 | Dantus et al. | |
| 2003/0143757 A1 | 7/2003 | Moore et al. | |
| 2003/0148391 A1 | 8/2003 | Salafsky | |
| 2006/0017999 A1 | 1/2006 | Vaughan et al. | |
| 2006/0187974 A1 | 8/2006 | Dantus | |
| 2006/0256332 A1 | 11/2006 | Sandstrom | |
| 2007/0152154 A1 | 7/2007 | Decamp et al. | |
| 2007/0171513 A1 | 7/2007 | Pannell et al. | |
| 2007/0291264 A1 | 12/2007 | Silberberg et al. | |
| 2009/0161092 A1 | 6/2009 | Zanni et al. | |

FOREIGN PATENT DOCUMENTS

| | | |
|---|---|---|
| WO | WO 97/18471 | 5/1997 |
| WO | WO 98/57155 | 12/1998 |
| WO | WO 02/27309 | 4/2002 |
| WO | WO 02/44730 | 6/2002 |
| WO | WO 03/002724 | 1/2003 |
| WO | WO 2004/031749 | 4/2004 |
| WO | WO 2006/033962 | 3/2006 |

OTHER PUBLICATIONS

The definition of "signal beam" from Wikipedia, the free encyclopedia. Printed on Oct. 1, 2009.*
Reed et al., Coherent Optical Photons from Shock Waves in Crystals. Physical Review Letters, 96, 013904, Jan. 13, 2006.*
Abramavicius et al. (2004) "Disentangling Multidimensional Femtosecond Spectra of Excitons by Pulse Shaping with Coherent Control," *J. Chem. Phys.* 120(18):8373-8378.
Asbury et al. (2003) "Ultrafast Heterodyne Detected Infrared Multidimensional Vibrational Stimulated Echo Studies of Hydrogen Bond Dynamics," *Chem. Phys. Lett.* 374:362-371.
Asplund et al. (2000) "Two-Dimensional Infrared Spectroscopy of Peptides by Phase-Controlled Femtosecond Vibrational Photon Echos," *Proc. Natl. Acad. Sci. USA* 97(15):8219-8224.
Bihan et al. (1996) "Determination of the Secondary Structure and Conformation of Puroindolines by Infrared and Raman Spectroscopy," *Biochem.* 35:12712-12722.
Blount et al. (2002) "The Hammerhead Ribozyme," *Biochem. Soc. Trans.* 30:1119-1122.
Bredenbeck et al. (2003) "Transient 2D-IR Spectroscopy: Snapshots of the Nonequilibrium Ensemble During the Picosecond Conformational Transition of a Small Peptide," *J. Phys. Chem. B* 107:8654-8660.

(Continued)

*Primary Examiner*—Frank W Lu
(74) *Attorney, Agent, or Firm*—Michael Best & Friedrich LLP

(57) ABSTRACT

This invention provides methods and devices for identifying and/or characterizing interactions involving molecules, including, but not limited to, identifying and/or characterizing interactions involving target molecules and candidate molecules. The present invention provides methods using multidimensional infrared spectrographic techniques, such as four wave mixing and pump-probe techniques, for identifying interactions involving biomolecules and therapeutic candidate molecules, and for characterizing such interactions in terms of their binding coefficients and/or equilibrium constants.

32 Claims, 14 Drawing Sheets

OTHER PUBLICATIONS

Chernyak et al. (1998) "Multidimensional Femtosecond Spectroscopies of Molecular Aggregates and Semiconductor Nanostructures: The Nonlinear Exciton Equations," *J. Chem. Phys.* 109(21):9587-9601.

Cho, M. (2001) "Nonlinear Response Functions for the Three-Dimensional Spectroscopies," *J. Chem. Phys.* 115(10):4424-4437.

Cho, M. (2003) "Two-Dimensional Circularly Polarized Pump-Probe Spectroscopy," *J. Chem Phys.* 119(11):7003-7016.

Cho, M. (2002) "Ultrafast Vibrational Spectroscopy in Condensed Phases," *Phys. Chem. Comm.* 5(7):40-58.

Choi et al. (2002) "Inter-Peptide Interaction and Delocalization of Amide I Vibrational Excitons in Myoglobin and Flavodoxin," *J. Chem. Phys.* 117:6821-6832.

Cohen et al. (1971) "Rate of Unwinding Small DNA," *J. Mol. Biol.* 61:525-542.

Demirdöven et al. (2002) "Correlated Vibrational Dynamics Revealed by Two-Dimensional Infrared Spectroscopy," *Phys. Rev. Lett.* 89(23):237401/1-237401/4.

Fecko et al. (2003) "Ultrafast Hydrogen-Bond Dynamics in the Infrared Spectroscopy of Water," *Science* 301:1698-1702.

Fulmer et al. (2004) "A Pulse Sequence for Directly Measuring the Anharmonicities of Coupled Vibrations: Two-Quantum Two-Dimensional Infrared Spectroscopy," *J. Chem. Phys.* 120(17):8067-8078.

Ge et al. (2002) "Local Structure and Dynamics of Liquid Acetone by Heterodyned 2D IR Spectroscopy," In; *Ultrafast Phenomena XIII*, Murane et al. eds., Springer-Verlag, pp. 592-594.

Gnanakaran et al. (2001) "Conformational Preferences and Vibrational Frequency Distributions of Short Peptides in Relation to Multidimensional Infrared Spectroscopy," *J. Am. Chem. Soc.* 123:12886-12898.

Gnanakaran et al. (2004) "Nature of Structural Inhomogeneities on Folding a Helix and Their Influence on Spectral Measurements," *Proc. Natl. Acad. Sci. USA* 101(25):9229-9234.

Golonzka et al. (2001) "Vibrational Anharmonicities Revealed by Coherent Two-Dimensional Infrared Spectroscopy," *Phys. Rev. Lett.* 86(10):2154-2157.

Ham et al. (2003) "Amide I Modes in the N-Methylacetamide Dimer and Glycine Dipeptide Analog: Diagonal Force Constants," *J. Chem. Phys.* 118(15):6915-6922.

Ham et al. (2004) Amide I Modes of Alpha-Helical Polypeptide in Liquid Water: Conformational Fluctuation, Phase Correlation, and Linear Nonlinear Vibrational Spectra,' *J. Phys. Chem. B* 108:9333-9345.

Ham et al. (2003) "Correlation Between Electronic and Molecular Structure Distortions and Vibrational Properties. II. Amide I Modes of NMA-$nD_2O$ Complexes," *J. Chem. Phys.* 118(8):3491-3498.

Hamm et al. (2000) "Pump/Probe Self Heterodyned 2D Spectroscopy of Vibrational Transitions of a Small Globular Peptide," *J. Chem. Phys.* 112(4):1907-1916.

Hamm et al. (1998) "Structure of the Amide I Band of Peptides Measured by Femtosecond Nonlinear-Infrared Spectroscopy," *J. Phys. Chem. B* 102(31):6123-6138.

Hamm et al. (2002) "Coupling of the Amide I Modes of the Glycine Dipeptide," *Bull. Chem. Soc. Jpn.* 75:985-988.

Hamm et al. (1999) "The Two-Dimensional IR Nonlinear Spectroscopy of a Cyclic Penta-Peptide in Relation to its Three-Dimensional Structure," *Proc. Natl. Acad. Sci. USA* 96:2036-2041.

Khalil et al. (2004) "Vibrational Coherence Transfer Characterized with Fourier-Transform 2D IR Spectroscopy," *J. Phys. Chem.* 121(1):362-373.

Khalil et al. (2003) "Obtaining Absorptive Line Shapes in Two-Dimensional Infrared Vibrational Correlation Spectra," *Phys. Rev. Lett.* 90(4):047401:1-4.

Krimm et al. (1986) "Vibrational Spectroscopy and Conformation of Peptides, Polypeptides, and Proteins," *Adv. Prot. Chem.* 38:181-364.

Krummel et al (2003) "Inter- and Intra-Strand Vibrational Coupling in DNA Studied with Heterodyned 2D IR Spectroscopy," *J; Phys. Chem. B* 107:9165-9169.

Merchant et al. (2002) "Frequency Selected Ultrafast Infrared Vibrational Echo Studies of Liquids, Glasses, and Proteins," *J. Phys. Chem. A* 106:8839-8849.

Moran et al. (2004) "The Origin of Vibrational Mode Couplings in Various Secondary Structural Motifs of Polypeptides," *Proc. Natl. Acad. Sci. USA* 101:506-510.

Moran et al. (2003) "Linear and Nonlinear Infrared Signatures of Local $\alpha$-and $3_{10}$- Helical Structures in Alanine Polypeptides," *J. Chem. Phys.* 118(8):3651-3659.

Mukherjee et al. (2004) "Site-Specific Vibrational Dynamics of the CD3zeta Membrane Peptide Using Heterodyned Two-Dimensional Infrared Photon Echo Spectroscopy," *J. Chem. Phys* 120(21):10215-10224.

Paul et al. (2004) "Vibrational Coupling, Isotopic Editing, and Beta-Sheet Structure in a Membrane-Bound Polypeptide," *J. Am. Chem. Soc.* 126:5843-5850.

Tian et al. (2003) "Femtosecond Phase-Coherent Two-Dimensional Spectroscopy," *Science* 300:1553-1555.

Piryatinski et al. (2001) "Vibrational-Exciton Relaxation Probed by Three-Pulse Echoes in Polypeptides," *Chem. Phys.* 266:285-294.

Rubtsov et al. (2003) "Dual-Frequency 2d-IR Spectroscopy Heterodyned Photon Echo of the Peptide Bond," *Proc. Nat. Acad. Sci. USA* 100(10):5601-5606.

Scheurer et al. (2001) "Design Strategies for Pulse Sequences in Multidimensional Optical Spectroscopies," *J. Chem. Phys.* 115(11):4989-5004.

Scheurer et al. (2002) "Infrared Analogs of Heteronuclear Nuclear Magnetic Resonance Coherence Transfer Experiments in Peptides," *J. Chem. Phys.* 116(15):6803-6816.

Scheurer et al. (2001) "Signatures of β-Peptide Unfolding in Two-Dimensional Vibrational Echo Spectroscopy: A Simulation Study," *J. Am. Chem. Soc.* 123(13):3114-3124.

Venkatramani et al. (2002) "Correlated Line Broadening in Multidimensional Vibrational Spectroscopy," *J. Chem. Phys.* 117(24):11089-11101.

Wang et al. (2004) "Characteristics of the Two-Dimensional Infrared Spectroscopy of Helices from Approximate Simulations and Analytic Models," *Chem. Phys.* 297:195-219.

Woutersen et al. (2000) "Structure Determination of Trialanine in Water Using Polarization Sensitive Two-Dimensional Vibrational Spectroscopy," *J. Phys. Chem. B* 104:11316-11320.

Yeremenko et al. (2003) "Hydrogen-Bond Dynamics in Water Explored by Heterodyne-Detected Photon Echo," *Chem. Phys. Lett.* 369:107-113.

Yuen et al. (1983) "Noise in Homodyne and Heterodyne Detection," *Opt. Lett.* 8(3):177-179.

Zanni et al. (2001) "Heterodyned Two-Dimensional Infrared Spectroscopy of Solvent-Dependent Conformations of Acetylproline-$NH_2$," *J. Phys. Chem. B* 105:6520-6535.

Zanni et al. (2001) "Two-Dimensional IR Spectroscopy can be Designed to Eliminate the Diagonal Peaks and Expose only the Crosspeaks Needed for Structure Determination," *Proc. Natl. Acad. Sci. USA* 98:11265-11270.

Zanni et al. (2000) "Frequency Resolved and Heterodyned Femtosecond Infrared Echos of Peptides; Multiple Pulse Coherent Vibrational Analogues of NMR," In;*Ultrafast Phenomena XII*, Elsaesser et al. Eds., Springer-Verlag, Berlin, pp. 504-506.

Zhao et al. (2000) "Doubly Vibrationally Enhanced Four Wave Mixing: The Optical Analog to 2D NMR," *Phys. Rev. Lett.* 84(7):1411-1414.

International Search Report and Written Opinion for Application No. PCT/US08/78582 dated May 27, 2009 (10 pages).

Belikov, R. et al., "Femtosecond direct space-to-time pulse shaping with MEMS micromirror arrays," Proceedings of IEEE/LEOS International Conference on Optical MEMS (Aug. 2003) 24-25.

Besemann, D. et al., "Experimental determinations of coherent multidimensional vibrational spectroscopy," Bull. Korean Chem. Soc. (2003) 24(8):1119-1125.

Ding, F. et al., "Heterodyned 3D IR spectroscopy," Chem. Phys. (2007) 341(1-3):95-105.

Ding, F. et al., "Passively correcting phase drift in two-dimensional infrared spectroscopy," Optics Letters (2006) 31(19):2918-2920.

Gallagher Faeder, S.M. et al., "Two-dimensional electronic correlation and relaxation spectra: theory and model calculations," J. Phys. Chem. A. (1999) 103:10489-10505.

Gnanakaran, S. et al., "Nature of structural inhomogeneities on folding a helix and their influence on spectral measurements," Proc. Natl. Acad. Sci. USA (2004) 101(25):9229-9234.

Grumstrup, E.M. et al., "Facile collection of two-dimensional electronic spectra using femtosecond pulse-shaping technology," Optics Express (2007) 15(25):16681-16689.

Hochstrasser, R.M. et al., "Two-dimensional spectroscopy at infrared and optical frequencies," Proc. Natl. Acad. Sci. USA (2007) 104(36):14190-14196.

Kaindl, R.A. et al., "Generation, shaping and characterization of intense femtosecond pulses tunable from 3 to 20 μm," J. Opt. Soc. Am. B. (2000) 17(12):2086-2094.

Keusters, et al., "Role of pulse phase and direction in two-dimensional optical spectroscopy," J. Phys. Chem. A (1999) 103:10369-10380.

Lacolle, M. et al., "Algorithms for the synthesis of complex-value spectral filters with an array of micromechanical mirrors," Optics Express (2006) 14(26):12590-12612.

Montgomery, M.A. et al., "General method for the dimension reduction of adaptive control experiments," J. Phys. Chem. A. (2006) 110:6391-6394.

Rabitz, H. et al., "Whither the future of controlling quantum phenomena?" Science (2000) 288:824-828.

Roth, M. et al., "Acousto-optical shaping of ultraviolet femtosecond pulses," Appl. Phys. B. (2005) 80:441-444.

Shim, S-H. et al., "Automated 2D IR spectroscoopy using a mid-IR pulse shaper and application of this technology to the human islet amyloid polypeptide," Proc. Natl. Acad. Sci. (2007) 104(36):14197-14202.

Shim, S-H. et al., "Femtosecond pulse shaping directly in the mid-IR using acousto-optic modulation," Optics Letters (2006) 31(6):838-840.

Shim, S-H. et al., "Generation and characterization of phase and amplitude shaped femtosecond mid-IR pulses," Optics Express (2006) 14(26):13120-13130.

Strasfeld, D.B. et al., "Controlling vibrational excitation with shaped mid-IR pulses," Phys. Rev. Lett. (2007) 99:038102-1-38102-4.

Tan, H-S. et al., "Mid infrared pulse shaping by optical parametric amplification and its application to optical free induction decay measurement," Optics Express (2003) 11(9):1021-1028.

Vaughan et al., "Coherently controlled ultrafast four-wave mixing spectroscopy," J. Physical Chem. A. (2007) 111(23):4873-4883.

Wagner, W. et al., "Rapid phase-cycled two-dimensional optical spectroscopy in fluorescence and transmission mode," Optics Express (2005) 13(10):3697-3706.

Weiner, A.M., "Femtosecond pulse shaping using spatial light modulators," Rev. Sci. Instruments (2000) 71(5):1929-1960.

Zanni, M.T., "New advances and applications of 2D IR spectroscopies: membrane peptides and coherent control," University of Pennsylvania Presentation given on Feb. 1, 2007, 93 pages.

Zanni, M.T., "New technology driving new science: mid-IR pulse shaping and automated 2D IR spectroscopy," ACS Presentation given on Mar. 24, 2007, 25 pages.

International Search Report and Written Opinion of the International Searching Authority for PCT/US05/32960 dated Jun. 19, 2008 (11 pages).

United States Patent Office Action for U.S. Appl. No. 11/963,123 dated Nov. 30, 2009 (20 pages).

Zanni, M. et al., "Vibrational tags for measuring distances and angles in biomolecules using 2D IR spectroscopy," Biophys. J. (2004) 86(1):322 A.

Zhao, W. et al., "Nonlinear two-dimensional vibrational spectroscopy," Applied Spectroscopy (2000) 54(7):1000-1004.

European Patent Office Search Report for Application No. 05812230 dated March 17, 2010 (6 pages).

* cited by examiner

NONLINEAR SPECTROSCOPIC METHODS FOR IDENTIFYING AND CHARACTERIZING MOLECULAR INTERACTIONS

CROSS-REFERENCE TO RELATED APPLICATIONS

This application claims priority under 35 U.S.C. 119(e) to U.S. provisional Patent Application 60/611,408 filed Sep. 20, 2004, which is hereby incorporated by reference in its entirety.

STATEMENT REGARDING FEDERALLY SPONSORED RESEARCH OR DEVELOPMENT

This invention was made with United States government support awarded by the following agencies: NSF 0130947. The United States has certain rights in this invention.

BACKGROUND OF THE INVENTION

Over the past decade, research in the field of proteomics has expanded tremendously due to its potential to revolutionize biological and medical research, particularly in the development of new drugs and therapies. The term proteome denotes an entire set of proteins that is encoded by a genome. The study of the proteome, called proteomics, is a complex interdisciplinary field of research directed at developing a functional description of gene and cellular activity in terms of the biological activities, interactions, localization, expression and modifications of proteins and protein complexes in cells and tissue.

The complexity of the field of proteomics is underscored by the very large number of proteins and protein complexes which correspond to a typical genome. The human proteome, for example, is considered to comprise between about 400,000 to about 1,000,000 proteins that interact to form an enormous number of protein complexes, many of which are believed to play fundamental roles in regulation of cellular activity and the onset of disease. This complexity is further compounded by the importance of a wide range of post-translational modification processes that profoundly affect protein tertiary structure, biological activity and cellular function.

As a result of the extraordinarily large number of proteins and protein complexes that participate in gene and cellular bioactivity, a variety of high throughput methods of probing protein interactions under conditions representative of cellular conditions have emerged over the last several years. Most of these techniques, genetic readout experiments such as the yeast two-hybrid assay, micro-array and chip experiments, mass spectrometry methods, and fluorescence based assay methods, take advantage of comprehensive genome and proteome databases that have become available in recent years. The available high throughput screening techniques provide complementary approaches to identifying and characterizing protein-protein interactions, protein-DNA interactions, protein-lipid interactions and post translational modifications that may be important in cellular activity. A fundamental goal of this aspect of proteomic research is to characterize cellular processes and the progression of disease in terms of networks of specific, identified protein interactions.

Networks of protein interactions developed from proteomic studies are particularly useful for identifying proteins and peptides that provide promising target molecules for the development of new drugs and therapies. Target proteins and peptides are molecules or components of molecules that are believed to participate in biochemical pathways associated with cellular development, regulation and/or the onset of disease. The composition, structure and reactivity of such target molecules are of great interest because surface targets may serve the basis of a drug therapy. For example, in vivo manipulation of the composition, conformation and/or biological activity of a protein involved in a select biochemical pathway, for example by administering a compound that inhibits, reduces or enhances its biological activity, may provide a mechanism for affecting cellular activity in a concerted manner. Target identification is typically followed by target validation studies, therefore, that confirm that manipulation of the selected target molecule has a desirable impact on cellular activity, such as the prevention of the progression of disease.

Recent availability of libraries of target protein and peptides generated via proteomic studies has stimulated considerable interest in developing new methods of identifying compounds that interact with target proteins or peptides and which may serve the basis of new and improved drugs and therapies. For example, substantial research efforts have been direct at concurrently developing rational, structure-based approaches and high throughput screening approaches for developing drugs and drug therapies from the abundance of available target protein and peptide data. Although these systematic methods employ fundamentally different approaches to identifying and refining therapeutic candidates, rational, structure-based methods and high-throughput methods are highly complementary techniques and are often used in combination wherein promising lead compounds are identified via high throughput methods and serve the basis of improved compounds developed by rational, structural based drug design methods.

In a rational, structure based drug design program, a small set of candidate molecules are developed based on known structural motifs of a selected target molecule or one of its natural ligands. The design of candidate molecules typically involves computer-based structure modeling of potential binding regions of the target molecule using databases of structural information. Eventually these techniques are used to derive a small subset of candidate molecules that are synthesized and evaluated to determine their reactivity with the target molecule and effect on its biological activity.

High-throughput screening approaches, in contrast, screen thousands of structurally diverse chemical compounds for binding activity with a selected target molecule in order to identify promising lead compounds that have potential as drugs. Most high throughput screening methods utilize an iterative process of screening a very large set of candidate compounds for activity, analyzing the results of the screen, and selecting a new set of compounds for additional screening based on properties elucidated from previous screens. Selection of compounds for additional screening is often driven by structure activity relationships (SARs) within the library screened compounds and using those relationships to further refine selection.

A large number of experimental strategies have evolved for target directed drug discovery via rational, structure-based drug design, high-throughput screening methods and the combination of these methods. A central component of each of these strategies, however, is sensitive methods of detecting and characterizing interactions between candidate molecules and target molecules. These methods must be capable of detecting a wide range of protein-ligand interactions, particularly weak protein-ligand interactions. Moreover, useful methods are also capable of characterizing protein-ligand interactions in terms of fundamental parameters important for evaluating the potential of a candidate compound to serve the basis of a drug therapy, such as the target binding affinity, inhibitory potential, region(s) of interaction, forward and reverse reaction rates and binding equilibrium constant. Methods that have been used to identify and evaluate lead candidate molecules include, fluorescent assays methods, mass spectrometry techniques, nuclear magnetic resonance (NMR) techniques, competitive binding assays, surface plasmon resonance methods and microarray functional assays.

Two-dimensional NMR (2D NMR) methods are currently a preferred technique for structurally characterizing proteins and probing interactions between target molecules and potential therapeutic candidates. 2D NMR methods differ from conventional one dimensional NMR methods in that more than one radio frequency pulse is applied to the sample, and the signal is measured as a function of direct and indirect time-delays. Fourier transform with respect to both the direct and indirect periods yields the two dimensional spectrum in frequency space having (i) diagonal peaks resulting from contributions of the magnetization that has not been changed by application of the additional radio frequency pulses and (ii) cross peaks originating from nuclei that exchanged magnetization during the mixing time subsequent to the application of the second radio frequency pulse. The intensity and position of cross peaks present in two dimensional NMR spectra indicate an interaction of two nuclei that exchanged magnetization and, therefore, contain additional, valuable information relating to structure. Other multidimensional NMR techniques, such as 3D NMR, have also be developed wherein a plurality of radio frequency pulses are delivered to a sample having pulse widths and time-delays selected to enhance the structure related information extracted from these measurements.

The introduction of an additional spectral dimension in 2D NMR spectroscopy results in spectra having additional structure related information. In addition, useful structural information may be more easily extracted from 2D spectra than in corresponding one dimensional NMR spectra of proteins, which are often extremely congested with many overlapping peaks. As a result of these advantages, a number of 2D homonuclear spectroscopic techniques have evolved for probing the structure of proteins, including 2D COSY, 2D TOCSY and 2D NOESY techniques which primarily differ in the pulses used during the mixing time. In addition, heteronuclear methods using $^{15}N$ and $^{13}C$ nuclei have also been developed as useful tools in elucidating protein structure. As the natural abundance of $^{15}N$ and $^{13}C$ is significantly lower than that of protons, these techniques often rely on isotope enrichment and enhancement of signal-to-noise ratios by use of inverse NMR methods wherein magnetization is transferred from protons to hetero nuclei.

In high-throughput and rational, structure based drug screening applications, 2D NMR spectra are generated corresponding to the target molecule or a labeled analog thereof in the absence of a therapeutic candidate molecule. In many applications, 2D $^{15}N/^{1}H$ heteronuclear single quantum correlation spectra are acquired because the $^{15}N/^{1}H$ signals corresponding to individual backbone amides of target proteins are often resolvable. Next, 2D NMR spectra are generated corresponding to the target molecule or a labeled analog thereof in the presence of a therapeutic candidate molecule, and compared to the spectra corresponding to the target molecule or a labeled analog thereof in the absence of a therapeutic candidate molecule. If measurable differences exist between the spectrum corresponding to the absence of the therapeutic candidate and the spectrum corresponding to the presence of the therapeutic candidate, a binding interaction may be inferred from the data. Furthermore, because shift values of $^{15}N/^{1}H$ signals in the 2D NMR spectra correspond to ascertainable locations within the target protein, quantitative analysis of the difference spectrum corresponding to the presence and absence of the therapeutic candidate may provide a means of identifying specific binding regions involved in the interaction. In some instances, a plurality of difference spectra corresponding to different concentrations of the candidate molecule may be analyzed to provide a measurement of the binding affinity and/or dissociation constant between a therapeutic candidate that binds with a target protein.

Although 2D NMR spectroscopy has been demonstrated to provide a useful screening method for identifying therapeutic candidate molecules that bind to proteins, these techniques are susceptible to certain drawbacks. First, 2D NMR spectra corresponding to proteins and protein mixtures take on the order of minutes (e.g. 10 minutes) to acquire. Furthermore, analysis of 2D NMR spectra requires operation of complex numerical simulating and fitting algorithms, which also take on the order of minutes to accomplish. As a result of these limitations, high-throughput screening candidate molecule libraries comprising thousands of compounds can take on the order of months to achieve. Second, the time resolution provided by 2D NMR spectroscopy is on the order of milliseconds and, thus, these methods are not capable of effectively detecting or characterizing transient binding interactions occurring on microsecond, picosecond and femtosecond timescales. Third, pulse radio-frequency beams used in NMR apparatus have longer wavelengths than other spectroscopic methods such as infrared spectroscopy, and so optical methods that simplify signal detection such as phase matching cannot be applied to NMR techniques. Finally, NMR is also a relatively insensitive technique and, thus, requires relatively large amounts of sample (about 0.1 to about 1 milliliters) as compared to optical spectroscopy techniques that are limited by the spot size (50 nanoliters). Such sample requirement considerations are compounded in NMR flow through experimental designs, wherein the relatively long sample intervals are needed to acquire a useful 2D NMR spectrum results in large sample volume requirements.

It will be appreciated from the foregoing that there is currently a need in the art for methods and devices for probing interactions involving biomolecules, such as proteins, peptides and DNA molecules that may serve as the basis of new drug therapies. Particularly, methods of screening interactions between proteins or components of proteins and potential therapeutic candidates are needed that are complementary to existing 2D NMR techniques. Screening methods capable of probing protein interactions occurring on sub-millisecond time scales are currently needed. In addition, improved methods of probing protein interactions requiring smaller sample volumes and shorter sampling intervals are needed to enable more efficient high-throughput screening applications.

SUMMARY OF THE INVENTION

The present invention provides methods and devices for detecting and characterizing interactions involving molecules, including biomolecules and potential therapeutic candidates. Screening methods are provided that are compatible with both high-throughput and rational, structure based approaches to drug discovery and optimization. It is an object of the present invention to provide methods and devices for detecting and characterizing interactions involving biomolecules occurring under conditions representative of in vivo conditions. It is further an object of the present invention to provide methods and devices for screening mixtures containing biomolecules and/or therapeutic candidates for the occurrence of potentially biologically significant interactions that provide an indication of either the occurrence of a binding interaction or the absence of a binding interaction significantly more rapidly than conventional high-throughput 2D NMR screening techniques and that have smaller sample volume requirements than conventional 2D NMR techniques. It is yet another object of the present invention to provide sensitive methods of detecting and characterizing interactions involving chemical species, such as biomolecules and/or potential therapeutic candidates, occurring on very short time scales, such as transient interactions occurring on sub-millisecond time scales.

In one aspect the present invention provides methods of using multidimensional vibrational and/or electronic spectroscopy techniques, such as two-dimensional infrared ("2D IR") spectroscopy for detecting and/or characterizing interactions between a first molecule and a second molecule, such as an associative interaction between a target molecule and a candidate molecule that resulting in formation of a molecular complex. Target and candidate molecules useful in this aspect of the present invention comprise molecules that absorb and/or scatter light in the infrared, visible and/or ultraviolet regions of the electromagnetic spectrum. Selection of target molecules and/or candidate molecules comprising biomolecules, however, provide particularly useful methods of detecting and/or characterizing interactions that may serve the basis of new therapies, such as drug and biological therapies. Biomolecules useful in these applications include, but are not limited to, proteins, peptides, DNA molecules, RNA molecules, oligonucleotides, lipids, carbohydrates, polysaccharides, glycoproteins, and derivatives, analogs, variants and complexes these including labeled analogs of biomolecules. In one embodiment of the present invention useful for identifying target molecules having potential to serve the basis of a drug discovery and/or drug design application, both target and candidate molecules are biomolecules or variants, analogs or derivatives thereof. In another application useful for identifying lead compounds, new therapeutic agents and/or improved therapeutic agents, the target molecule comprises a biomolecule or variant, analog or derivative thereof and the candidate molecule is a potential therapeutic candidate or variant, analog or derivative thereof, such as molecule having potential as a pharmaceutical or biological agent. In another application useful for evaluating the potential of a therapeutic candidate or lead compound to interact with other therapeutic agents, the target molecule comprises a therapeutic candidate or variant, analog or derivative thereof and the candidate molecule is a known therapeutic agent or a metabolite thereof.

In one embodiment of this aspect of the present invention, methods and devices are provided which use multidimensional vibrational and/or electronic spectroscopy techniques, such as 2D IR, electronic, Raman and hyper Raman spectroscopy techniques, to monitor intermolecular and intramolecular coupling between vibrational modes and/or electronic states of a first molecule, second molecule or both for identifying the occurrence of an interaction or the absence of an interaction involving the first molecule and the second molecule. A first molecule is provided and contacted with a second molecule. Coherent light of a first selected wavelength and coherent light of a second selected wavelength that is different from the first selected wavelength are directed onto the first molecule, second molecule or both and coherently excite molecular vibrations in the first molecule, the second molecule or both. In one embodiment, the first selected wavelength is resonant with a first vibrational mode of the first molecule and the second selected wavelength is resonant with a second vibrational mode of the first molecule. In an alternative embodiment, the first selected wavelength is resonant with a first vibrational mode of the second molecule and the second selected wavelength is resonant with a second vibrational mode of the second molecule. In one embodiment useful for identifying molecules having potential as a drug and/or biological, the first molecule comprises a target molecule and the second molecule comprises a candidate molecule.

In the present methods, coherent excitation of the first molecule, second molecule or both results in generation of one or more a signal beams. Signal beams in the present methods result, at least in part, from intermolecular and intramolecular processes that couple vibrational motions corresponding to vibrational states excited in the first molecule, second molecule or both. These processes include electrostatic interactions, and steric (i.e. mechanical) interactions between atoms participating in vibrational motions in the first molecule, second molecule or both and also include vibrational energy relaxation processes. As an interaction between the first molecule and the second molecule has potential to substantially affect the local electrostatic and/or steric environments of atoms participating in motion corresponding to these vibrational modes, changes in measurable properties of the signal beam, such as the intensity, amplitude and/or time dependence of the electric field, polarization state and propagation direction, provide information directly related to the occurrence, structural nature and nature of the interaction. For example, changes in the local electrostatic and/or steric environments of atoms participating in motion corresponding to these vibrational modes due to interaction of the first and second molecules induces corresponding changes in the energy levels of the vibrational modes, changes in the vibrational linewidths, and changes in vibrational energy relaxation processes that are available to the vibrationally excited first molecule, second molecule or both. Detection of signal beams in the present invention provides a means of identifying and quantifying these changes in energy levels and vibrational energy relaxation processes, which in turn provides a sensitive means of identifying the occurrence of and/or characterizing the fundamental nature of interactions between first and second molecules.

This aspect of the present invention is particularly useful for probing changes in energy levels and vibrational energy relaxation processes that accompany an associative interaction between a first molecule comprising a target molecule and a second molecule that comprises a candidate molecule. In such an interaction, a target molecule and a candidate molecule can associate in a manner resulting in formation of a molecular complex having its own vibrational modes and vibrational energy states, some of which are substantially different from the vibrational modes of the isolated target molecule and/or candidate molecule. Furthermore, associative interactions bring together atoms participating in discrete vibrational motions associated with vibrations excited in the target molecule with atoms participating in discrete vibrational motions associated with vibrations excited in the candidate molecule. In an associative complex resulting from binding of target and candidate molecules, therefore, the vibrational motions corresponding to the vibrational modes often experience different electrostatic and steric environments, which result in measurable changes in properties of the signal beam. Such changes in the electrostatic and steric environments of an excited vibrational mode may even occur when the interaction between candidate molecule and target molecule occurs in a region of the target molecule or candidate molecule not localized proximate to (i.e. is far away from) the excited vibration modes, such as on the other end of a large protein or peptide.

In one embodiment of the present invention particularly useful for high throughput applications, experimental conditions are selected such that the signal beam propagates along an axis spatially separated from the propagation axes of the coherent light of the first selected wavelength and the coherent light of the second selected wavelength. In this embodiment, the signal beam is detected at a specific detection angle defined by the intersection of the propagation axis of the signal beam and the propagation axis of coherent light of a first selected wavelength, coherent light of a second selected wavelength or both. For example, the present invention include methods wherein the signal beam results from the interaction of the coherent light of the first selected wavelength, the coherent light of the second selected wavelength or both with an induced refractive index grating formed by optical interference of the coherent light of the first selected wavelength and the coherent light of the second selected wavelength. Alternatively, the present invention includes methods wherein the signal beam propagates along propagation axes which are substantially coincident with the propagation axes of the coherent light of the first selected wavelength, the coherent light of the second selected wavelength or both. The detected signal beam is strongest in the spatial direction set by phase matching conditions that depend on the wavelengths and spatial geometries of the coherent light from the first and second wavelengths, but does not have to be detected along these directions. Phase matching is useful for some applications of the present methods but is not necessary.

In this aspect of the present invention, the occurrence of an interaction or absence of an interaction involving the target molecule and the candidate molecule is identified by detecting the signal beam. In one embodiment, the intensity, amplitude, time dependence and/or polarization of the electric field of the signal beam is measured for experimental conditions corresponding to the target molecule in the absence of the candidate molecule (i.e. prior to the step of contacting the target molecule with the candidate molecule), thereby determining a first measurement, such as a first intensity ($I_1$) and/or first amplitude of the electric field ($E_1$), and the intensity, amplitude, time dependence and/or polarization of the electric field of the signal beam is measured for experimental conditions corresponding to the target molecule in the presence of the candidate molecule (i.e. after to the step of contacting the target molecule with the candidate molecule), thereby determining a second measurement, such as a second intensity ($I_2$) and/or second amplitude of the electric field ($E_2$). First and second measurements are compared, for example by determining the difference between first and second intensities ($I_1-I_2$) and/or first and second amplitudes of the electric field of the signal beam ($E_1-E_2$). A measurable difference in first and the second measurements, such as measurable differences in intensities of the signal beam ($I_1-I_2$) and/or measurable differences in the first and the second amplitudes of the electric field of the signal beam ($E_1-E_2$), indicates the occurrence of an interaction involving the target molecule and the candidate molecule. A similar comparison process can be done with a sample of pure solvent to determine whether signal from the solvent and/or non-resonance signal and/or background from the sample holder contributes to the measurement.

Conceptually, at least a component of the differences in first and second measurements may be regarded as arising from changes in intramolecular and intermolecular processes that couple atomic motions corresponding to the vibrational modes and states excited in the target molecule and/or the candidate molecule due to the occurrence of an interaction between these species, such as an associative interaction, wherein the candidate molecule and target are brought into and held in close proximity. In contrast, first and second intensities and/or amplitudes that are observed to be identical, within their respect uncertainties, indicate the absence of an interaction involving the target molecule and the candidate molecule. Under these conditions, the intramolecular and intermolecular processes that couple atomic motions corresponding to the vibrational states excited in the target molecule and/or the candidate molecule remain unchanged. An additional benefit of this method of the present invention is that measured differences in first and second intensities and/or amplitudes also provides quantitative information relating to the fundamental nature of and molecular dynamics involved in the interaction between target molecule and candidate molecule, such as the magnitude of the binding affinity or dissociation constant.

In an alternative embodiment of the present invention, coherent light having a first selected wavelength resonant with a vibrational mode of the target molecule and coherent light having a second selected wavelength resonant with a vibrational mode of the candidate molecule is directed onto the target molecule, candidate molecule or both. In an embodiment useful for high-throughput screening applications, first and second selected wavelengths are selected such that a signal beam is only generated if the vibrational mode excited in the target molecule is coupled to the vibrational mode excited in the candidate molecule, for example by an associative interaction between these species. Accordingly, detection of a measurable signal beam in this embodiment of the present invention indicates the occurrence of an interaction involving the target molecule and the candidate molecule that results in coupling of the intra-atomic motions corresponding to the vibrational modes excited. In contrast, if no measurable signal beam is generated, an absence of an interaction involving the target molecule and the candidate molecule may be inferred. Methods of the present invention capable of generating a signal beam propagating along an axis that is spatially separated from the propagation axes of the incident coherent light of first and second selected wavelengths, for example establishing an induced index of refraction grating through phase matching by interaction of the coherent light having the first selected wavelength and coherent light having the second selected wavelength, are particularly well suited for this embodiment of the present invention because the presence of or absence of such a spatially separated signal beam may be easily determined with out the need for wavelength filter methods by merely detecting the presence or absence of the signal beam propagating along a selected detection axis. This embodiment of the present invention is particular well suited for high-throughput screening applications because very little signal analysis is required to determine if an interaction has taken place, other than ensuring any signal detected is above the relevant noise levels. Use of ultra sensitive infrared detectors including, but not limited to, mercury cadmium telluride detectors, are beneficial for some applications of this aspect of the present invention, particularly those applications involving screening candidate molecules for weak interactions with a target molecule. Array detectors and balanced single channel or array detectors are also suitable for such applications of the present invention.

In another alternative embodiment, a method of the present invention comprises a competitive binding screening method for identifying an interaction involving a target molecule and a candidate molecule, such as an interaction wherein the candidate molecule partially displaces or completely displaces a competitive binding reference molecule bound to the target molecule. An exemplary method of this aspect of the present invention further comprises the step of contacting the target molecule with a competitive binding reference molecule prior to the step of contacting the target molecule with a candidate molecule, thereby binding the target molecule to the competitive binding reference. Competitive binding reference molecules useful in this aspect of the present invention are molecules that are known to bind, at least to some extent, to the target molecule, and in some embodiments comprise a known drug, biological therapeutic or lead compound in a drug discovery program.

In one embodiment of this method, coherent light having a first selected wavelength that is resonant with a vibrational mode of the target molecule and coherent light having a second selected wavelength resonant with a vibrational mode of the competitive binding reference molecule is directed at the target molecule, competitive binding reference molecule or both. A first signal beam at least partially arising from coupling of intermolecular and intramolecular motions corresponding to vibrational modes excited in the target molecule and competitive binding reference molecule complex is generated and detected, for example by measuring the intensity and/or amplitude of the electric field of the signal beam. A candidate molecule is then brought into contact with the target molecule bound to the competitive reference molecule and a second signal beam corresponding to these experimental conditions is detected.

Observable changes in first and second signal beams, provides an indication of an interaction involving a target molecule and a candidate molecule, such as an interaction wherein the candidate molecule partially or completely displaces the competitive bind reference molecule bound to a target molecule. Conceptually this may be regarded as arising from changes in the steric and electrostatic environment of target molecule and competitive binding reference molecule that affects coupling between intramolecular and intermolecular motions corresponding to vibrational modes excited in these species. An additional benefit of this method of the present invention is that measured differences in first and second signal beams, such as differences in intensity and/or amplitude of electric field, also provides quantitative information relating to the nature of an interaction between target molecule and candidate molecule, such as the magnitude of the binding affinity.

In some embodiments of this aspect of the present invention, coherent light having a first selected wavelength, coherent light having a second selected wavelength or both comprise one or more coherent pulses of electromagnetic radiation, such as coherent infrared laser pulses having femtosecond, picosecond or nanosecond temporal widths. In one embodiment, coherent light having a first selected wavelength and coherent light having a second selected wavelength comprise a single coherent pulse of electromagnetic radiation having a temporal profile with at least two maxima. For example in a method of the present invention useful for providing a spatial separated signal beam, coherent light having a first selected wavelength and coherent light having a second selected wavelength comprise a single coherent pulse of electromagnetic radiation with a selected temporal profile having a plurality of maxima wherein the time between maxima is selected and/or selectively adjustable. In an alternative embodiment also useful for providing a spatially separated signal beam, coherent light having a first selected wavelength comprises a first coherent pulse of electromagnetic radiation provided to the target molecule, candidate molecule, competitive binding molecule or any combination of these at a first time corresponding to the first pulse of electromagnetic radiation. Coherent light having a second selected wavelength comprises a second coherent pulse of electromagnetic radiation provided to the target molecule, candidate molecule, competitive binding molecule or any combination of these at a second time that is a selected delay time after the first time. In these aspects of the present invention, the selected time between maxima in the temporal profile of a single coherent pulse of electromagnetic radiation or the delay time between first and second coherent pulses of electromagnetic radiation can be scanned, selectively adjusted or selected and held at a constant value on the basis of the vibrational modes that are excited and the corresponding intramolecular and intermolecular processes that couple these vibrational modes.

The present invention includes embodiments wherein additional coherent pulses of electromagnetic radiation, such as third, fourth and fifth coherent pulses of electromagnetic radiation, are provided to the target molecule, candidate molecule, competitive binding reference molecule or any combination of these. These embodiments include multidimensional IR spectroscopic techniques, multidimensional Raman spectroscopic techniques and multidimensional hyper-Raman spectroscopic techniques In an embodiment useful for high-throughput screening and rational, structure based drug design applications, additional coherent pulses of electromagnetic radiation comprising laser pulses, such as femtosecond infrared laser pulses, picosecond infrared laser pulses and/or nanosecond infrared laser pulses, are provided to the target molecule, candidate molecule, competitive binding reference molecule or any combination of these at selected delay times after a first time corresponding to a first coherent pulse of electromagnetic radiation. Delay times useable in this embodiment of the present invention may be scanned, selectively adjustable or selected and held at a constant value.

Methods of this aspect of the present invention may further comprise the step of providing a target molecule, candidate molecule, competitive binding reference molecule or any combination of these having one or more a vibrational tags, preferably for some application a vibrational tag(s) having a resonance frequency that does not overlap significantly with the resonance frequencies of other vibrational modes of the target molecule, candidate molecule, competitive binding reference molecule or any combination of these. In one embodiment, a vibrational tag is added to a molecule such that the molecule labeled with the vibrational tag has at least one new vibrational mode of a selected resonance frequency, preferably for some application a selected resonance frequency that does not significantly overlap with the frequencies of the other vibration modes of the molecule. Vibrational tags preferred for some screening applications, such as methods of identifying the presence or absence of an interaction involving a protein or peptide, do not significantly affect the overall tertiary structure or reactivity of the molecule labeled with the vibrational tag. In some aspects of the present invention, the composition of the vibrational tag is selected such that the biological activity of the molecule labeled with the vibrational tag is equivalent to the biological activity of the molecule without the vibrational tag.

Vibrational tags of this embodiment, comprise atoms and/or groups of atoms that are added to the molecule, such as atoms or groups of atoms that are covalently bound to or electrostatically incorporated into the molecule, that affect the absorption of light by the molecule, such as absorption of light in the infrared, visible and ultraviolet regions of the electromagnetic spectrum. Candidate molecules, target molecules and/or competitive binding reference molecules having a vibrational tag may also comprise a sample that is enriched with a selected stable isotope, such as deuterium, sulfur-34 ($^{34}$S) carbon-13 ($^{13}$C), or oxygen-18 ($^{18}$O). Exemplary atoms and groups of atoms providing useful vibrational tags for proteins and peptides have resonance frequencies selected over the range of about 1900 cm$^{-1}$ to about 2300 cm$^{-1}$ and include groups having triple bond character and cumulated double bond character. Exemplary tags for proteins and peptides include, but are not limited to, a azido groups (—N=N=N$^-$), aliphatic diazo groups (C=N=N), cyano groups (—C≡N), cynate groups, (—N=C=O), thiocynates (—N=C=S; —S—C≡N), ketene groups (C=O=O), isocyanate groups (—N=C=O), isothiocyanate groups (—N=C=S), aminonitriles (N—C≡N), isonitrile groups (—N≡C), carbonyl groups (—C=O), mono-substituted acetylene groups (—C≡C—H), di-substituted acetylene groups (—C≡C—), nitrile groups (—CH$_2$—C≡N), acrylonitriles (—C+C—C≡N) or any combination of these. An advantage of these vibration tags is that they absorb in a region of the infrared spectrum wherein adsorption of light by many peptides and proteins is low (e.g. optical density less than about 500 per mole$^{-1}$ per cm$^{-1}$). Exemplary atoms and groups of atoms also providing useful vibrational tags may also comprise groups having one or more stable isotopes exhibiting a significant shift in resonance frequency relative to the resonance frequency of other more common isotopes, such as groups having one or more C-D bond, one or more C=$^{34}$S bonds, one or more C=$^{18}$O bonds or combinations of these.

An advantage of vibrational tags useful in the present invention is that they typically, but do not have to, comprise small numbers (< about 4 atoms) of relatively small atoms (atomic number < about 8), which have small, if any, effects on structure, reactivity and biological activity, but have relatively large effects on the IR spectrum of the of molecules labeled with the vibrational tags, such as provide strong, new absorptions. This advantage of the present invention is in contrast with fluorescent tags used in fluorescence based assay methods, which are typically much larger groups of atoms and thus, often have significant impacts on the structure, reactivity and biological activity of molecules labeled with fluorescent tags.

Use of vibrational tags in the methods of the present invention is beneficial because it allows for coherent excitation of vibrational modes of a target molecule, candidate molecule, competitive binding reference molecule or any combination of these at resonance frequencies that do not overlap significantly with the resonance frequencies of other vibrational modes of the target molecule, candidate molecule, competitive binding reference molecule or any combination of these present in a sample undergoing analysis. In the context of one aspect of the present invention, with the proper choice of resonance frequencies, infrared pulse intensities, and phase matching detection, use or absence of a heterodyned pulse, and concentrations of target, candidate molecule, competitive binder or vibrational tags, resonance frequencies that do not overlap significantly have oscillator strengths greater than or equal to as little as 1.01 times the oscillator strength of other overlapping resonance frequencies. Accordingly, vibrational tags in the present invention allow energy to be introduced into a sample undergoing optical analysis in a well controlled and pre-selected manner. For example, use of one or more vibrational tags may be used to selectively and coherently excite one or more vibrational modes corresponding to one or more vibrational tags on a protein or peptide without significantly exciting other vibrational modes of the protein or peptide.

In one embodiment, methods of the present invention further comprise the steps of: (1) optionally providing a target molecule having a vibrational tag, (2) optionally providing a target molecule having a vibrational tag, (3) optionally providing a competitive binding reference molecule having a vibrational tag; (4) selecting coherent light of the first wavelength resonant with a vibration mode corresponding to a vibrational tag of a target molecule, candidate molecule and/or competitive binding reference molecule, and (5) optionally selecting coherent light of a second wavelength resonant with a vibration mode corresponding to a vibrational of a target molecule, candidate molecule and/or competitive binding reference molecule.

In another aspect, the present invention provides methods of characterizing an interaction between a target molecule and a candidate molecule. In one embodiment, a method of the present invention comprises the steps of providing a target molecule and generating a first multidimensional vibrational spectrum, such as a 2D IR spectrum, corresponding to experimental conditions of the target molecule in the absence of a candidate molecule. The target molecule is contacted with a candidate molecule and a second multidimensional vibrational spectrum, such as 2D IR spectrum, is generated corresponding to experimental conditions of the target molecule in the presence of the candidate molecule. First and second multidimensional vibrational spectra, such as 2D IR spectra, are compared, for example by generating a 2D IR difference spectrum. Measurable differences in first and second multidimensional vibrational spectra, indicate the occurrence of an interaction(s) between target and candidate molecules and provide quantitative information regarding the fundamental nature of and molecular dynamics involved with the interaction. For example, differences in first and second multidimensional vibrational spectra may be attributed to changes in the steric and/or electrostatic environments of specific, identifiable atoms that participate in vibrational motions corresponding to vibrational modes excited in target and candidate molecules. In one embodiment of the present invention, changes in first and second 2D IR spectra, such as shifts in the positions and intensity distributions of cross peaks and the appearance of new cross peaks, may be used to identify one or more regions of the target molecule, candidate molecule or both that participate in the interaction. This technique may also be used to probe the resulting structure of a molecular complex formed by associative interaction of the target molecule and candidate molecule. An advantage of this method of the present invention is that it provides useful structural information relating to a target-candidate interaction, such as the localization, composition and structure of a binding region(s) of the target molecule and/or candidate molecule that is useful in assessing the biological importance of the interaction in a drug discovery or optimization program.

In another embodiment, the present methods of characterizing an interaction between a target molecule and a candidate molecule comprise a method of determining the binding constant, dissociation constant or equilibrium constant corresponding to an associative interaction between the target molecule and the candidate molecule. In one embodiment, a plurality of multidimensional vibrational spectra, such as 2D IR spectra, are acquired corresponding to experimental conditions wherein the concentration of the candidate molecule is selectively varied over a selected concentration range. This method of the present invention, further comprises the step of separately contacting the target molecule to various, selected concentrations of the candidate molecule and measuring a multidimensional vibrational spectrum, such as 2D IR spectrum, corresponding to each candidate molecule concentration. In one embodiment, a plurality of difference spectra are determined by comparing the 2D IR spectrum corresponding to each candidate molecule concentration from a 2D IR spectrum corresponding to experimental conditions of the target molecule in the absence of the candidate molecule. An advantage of this method of the present invention is that it provides direct measurements of fundamental properties, such as binding constants and dissociation constants, that are useful for evaluating the biological significance of an interaction and/or potential of a candidate molecule to provide a lead compound in a drug discovery or optimization program.

Multidimensional vibrational and electronic spectra, such as 2D IR spectra, useable in the present methods may be generated by any means known in the art of infrared spectroscopy. "Ultrafast vibrational spectroscopy in condensed phase," Phys. Chem. Comm., 2002, 5(7) p. 40-58, m by Minhaeng Cho and "Dual-frequency 2D-IR spectroscopy heterodyned photon echo of the peptide bond," Proc. Natl. Acad. Sci. USA 2003 100 (10): 5601-5606, by Rubtsov et al., Golonzka O, Khalil M, Demirdöven N, Tokmakoff A. *Phys. Rev. Lett.* 2001, 86, 2154, "Experimental Determinations of Coherent Multidimensional Vibrational Spectroscopy," Bull. Korean Chem. Soc., 2003, Vol. 24, No. 8 1119-1125 by Besemann et al. and "Two-dimensional IR spectroscopy can be designed to eliminate the diagonal peaks and expose only the cross peaks needed for structure determination," *Proc. Natl. Acad. Sci. USA* 2001, 98, 11265 by Zanni et al. provide descriptions of multidimensional vibrational spectroscopy methods and means of generating multidimensional vibrational spectra, such as 2D IR spectra. These references are hereby incorporated by reference in their entireties. Means of generating multidimensional vibrational spectra, such as 2D IR spectra, useful in the methods of the present invention involve measurement of the time dependence signal (e.g. intensity or amplitude of electric field) of the signal beam under experimental conditions corresponding to selective variation of the frequency of coherent of light delivered to a target containing sample, selective variation of the temporal properties of coherent pulses of electromagnetic radiation delivered to a target containing sample, such as selective variation of delay times between pulses of coherent electromagnetic radiation, and/or selective variation of the polarization states of coherent light provided to a target containing sample. Exemplary means of generating multidimensional vibrational spectra, such as 2D IR spectra, useable in the present methods include four wave mixing techniques and pump-probe methods including, but not limited to, two pulse photon echo techniques, three pulse photon echo techniques, heterodyned four wave mixing techniques, homodyne four wave mixing techniques, dual frequency heterodyned transient grating techniques, frequency resolved four wave mixing techniques, spectrally resolved four wave mixing techniques, pulse shaping four wave mixing techniques, narrow band (picosecond) four wave mixing techniques, broad band four wave mixing techniques, time-gated four wave mixing techniques, and any version(s) of the above techniques with linearly or circular polarized pulses and temporally and/or wavelength shaped pulses. The present methods also include techniques based on six-wave, eight-wave and higher variants are also included, as are variants that are not well described by a perturbative description or ones that include both n-wave and m-wave mixing where n and m are integers. It is well-known that many of the coherent, multidimensional vibrational and electronic processes and techniques referred to above have incoherent analogues. Description of coherent multidimensional techniques in the present methods is by way of example, and incoherent analogues of these techniques are also useful for carrying out the methods of the present invention. Accordingly, the present invention includes all variations of the present methods wherein incoherent analogues are substituted for the coherent, multidimensional techniques and processes described and referred to in this description.

The methods of the present invention are compatible with high-throughput drug screening applications, structure based drug development and optimization applications and high throughput proteomic assays for identifying biologically significant protein-protein interactions and determining protein interaction networks. In one embodiment, the present methods further comprise the step of separately contacting the target molecule with a plurality of different candidate molecules, for example separately contacting the target molecule with different candidate molecules, for example in microwells in a microarray system or in a microfluidic or nanofluidic channel. In this embodiment, the occurrence of interactions involving the target molecule and any of the different candidate molecules is identified and/or characterized. The present methods are particularly useful for high-throughput applications because only small amounts of target molecule and candidate molecule are required, for example nanomolar quantities, to evaluate each potential interaction and because the occurrence of each potential interaction may be probed and analyzed very quickly. In some embodiments of the present invention, the rate at which interactions may be probed may be established by the repetition rate of the laser, which at present is on the order of millisecond or sub-millisecond time scales, and which expect to decrease a instrumentation in this field continues to advance. In addition, the present methods are well suited for both high throughput and structure based drug discovery and optimization programs because they allows for detection and characterization of transient interactions occurring on very fast time scales, such as microsecond, picosecond and femtosecond time scales, that may play important role in biological pathways and in the development of new therapies.

The present invention provides methods for analyzing substantially pure samples, for example mixtures comprising substantially pure mixtures of a target molecule, a candidate molecule, competitive binding reference molecule or a combination of these. Alternatively, the present invention provides methods for analyzing complex mixtures of one or more candidate molecule, one or more competitive binding molecule, one or more competitive binding reference molecule and/or impurities present in the mixture. Particularly, the present methods provide methods probing interactions between a selected target molecule and a selected candidate molecule in the presence of other materials such as solvents, including water, buffers, ions and impurities. Solvents useful in the present methods include, but are not limited to, isotopically labeled solvents such as $D_2O$ or deuterated alcohols, which may be used to remove background absorption or background signal. In one embodiment, the high degree of selectivity in the present invention is provided by selection of the frequency distributions of coherent excitation pulses that are principally, if not exclusively absorbed, by a selected target molecule, candidate molecule or competitive binding reference molecule. Selectivity may also be provided by selection of appropriate polarization states and/or temporal profiles of coherent excitation pulses and by selection of the appropriate delay times between coherent excitation pulses. One of the key advantages of the enhanced selectivity provided by optical analysis using multiple spectral dimensions is that this approach provides an effective means of reducing spectral congestion and overlapping spectral lines that are problematic in one-dimensional vibrational and electronic spectroscopic analysis of large biomolecules. An advantage of the present invention is that target molecule-candidate interactions can be probed under solution conditions, such as pH, ionic strength etc., representative of in vivo conditions.

The present methods may be used to identify and/or characterize interactions between target and candidate molecules flowing in a flow-through system, for example flow through systems wherein the target molecule, candidate molecule, competitive binding reference molecule or combinations of these are continuously flowed or mechanically pulsed through an optical analysis region. Alternatively, present methods may be used to identify and/or characterize interactions occurring in a static reaction region, such as a microwell in a microarray apparatus. In one embodiment of this aspect of the present invention, one or more optical sources are scanned to provide coherent light of selected first and second wavelengths to different regions of a microarray apparatus. In an alternative embodiment, coherent light of selected first and second wavelengths is simultaneously provided to different regions of a microarray apparatus.

The present methods are capable of identifying and/or characterizing target, candidate, or both target and candidate molecules in a wide variety of chemical and physical environments. Measurements can be performed in a variety of different kinds of solvents such as water, $D_2O$, hydrophobic solvents, hydrophilic solvents, and organic solvents. Furthermore, the methods is capable of identifying and/or characterizing target, candidate, or both targets and candidates in membrane samples, vesicle samples, bilayer samples, micelle samples and other types of cellular models. The targets and/or candidates can be membrane bound or membrane associated proteins or peptides. The compatibility of the present techniques with membrane bound or surface bound molecules results principally from fact that the resolution of the technique is not dependent on the rotational motion of the molecules being analyzed. This beneficial aspect of the present invention is in contrast with multidimensional NMR techniques, wherein solution phase measurements are severely hindered by line broadening caused by constraints on rotational motion introduced to a molecule when it is bound to a membrane structure or other large substrate. In addition, the methods can be used to probe crystalline structures as well, for example, the crystal structures used in x-ray diffraction. Furthermore, they can be used in glasseous environments such as trehalose glass.

In the present invention, the target molecule, candidate molecule, competitive binding reference molecule or combinations of these may be provide in any manner capable of providing contact between these molecules. In one aspect of the present invention useful for high-throughput screening methods, a plurality of different candidate molecules are provided on different polymer beads and are contact separately with target molecules. Alternatively, target molecule, candidate molecule, competitive binding reference molecule or combinations of these may be provided in static reaction vessels, such as at least partially transparent microwells in a microarray system or transparent glasses substrates, such as polymer glass substrates. Alternatively, target molecule, candidate molecule, competitive binding reference molecule or combinations of these may be provided in a channel of a flow-through system, such as in a microfluidic channel of a microfluidic system or a nanofluidic channel of a nanofluidic system.

The present methods are capable of identifying and/or characterizing a wide variety of interactions, such as interactions that involve target molecule and candidate molecule. The term "interaction" refers to physical and/or electrostatic contact processes involving one or more moieties that have a measurable effect on the structure and/or composition of at least one molecule participating in the interactions. In one aspect of the present invention, the term "interaction" refers to a measurable chemical or physical interaction between a target molecule and a candidate molecule that is capable of affecting the structure and/or composition of a target molecule, a candidate molecule or both such that the biological activity of the target molecule, a candidate molecule is affected. Interactions capable of affecting the structure and/or composition of a molecule include, but are not limited to, reactions resulting in the formation of one or more covalent bonds, resulting in the breaking of one or more covalent bonds, electrostatic associations and repulsions, formation and/or disruption of hydrogen bonds, formation and/or disruption of electrostatic forces such as dipole-dipole interactions, formation and/or disruption of van der Waals interactions or processes comprising combinations of these. The present methods are capable of identifying and/or characterizing interactions of a candidate molecule that inhibits the biological activity of the target molecule, decreases the biological activity of the target molecule or enhances the biological activity of the target molecule. The present methods are useful for identifying and/or characterizing associative interactions between a target molecule and a candidate molecule, such as an associative interaction of a therapeutic candidate and a biomolecule.

In addition, present methods are useful for identifying and/or characterizing transient interactions involving a target molecule that results in a change in composition, structure and/or biological activity. For example, the method of the present invention may be used to identify and characterize post-translational and co-translational modifications of proteins and peptides, such as proteolytic cleavage reactions, glycosylation reactions, phosphorylation reactions, acetylation reactions, hydroxylation reactions, methylation reactions and nucleotidylylation reactions. In one embodiment, the methods of the present invention are capable of identifying regions of a protein or peptide that have undergoing a change in composition. In addition, the methods of the present invention are useful for characterizing changes in the tertiary structure caused by changes in solution conditions, such as pH, ion strength and temperature. The methods of this aspect of the present invention may be used in combination with other complementary techniques for identifying and characterizing structural changes, such 2D NMR techniques.

The present invention also comprises methods of identifying and/or characterizing interactions involving molecules using multidimensional electronic spectroscopy techniques. In these methods one or more electronic transitions are coherently excited by coherent light having a first selected wavelength and/or coherent light having a second selected wavelength. In one embodiment, selected vibrational transitions are coherently excited in a target molecule and candidate molecule using first and second coherent excitations pulses. One or more electronic transitions in the target molecule, candidate molecule are also coherently excited, thereby generating a signal beam comprising visible or ultraviolet light. Detection of the signal beam allows the occurrence or absence of interactions between the target and candidate molecules to be determined. An advantage of techniques of this aspect of the present invention is that very sensitive detectors suitable for visible light, such as photomultiplier tubes and photodiodes, may be used to determine the intensity and/or amplitude of the electric field of the signal beam. Furthermore, signal beams having wavelengths in the visible and ultraviolet light regions may be optically filtered effectively using available filtering devices such as monochrometers, dispersive elements and optical interference filters.

The methods of the present invention are complementary, to many existing high-throughput screening methods and rational, structure based drug discovery and optimization methods. In one embodiment, for example, the present invention provides a high-throughput preliminary screening tool wherein a plurality of candidate molecules, such as a library of 1000 s to 100,000 s of therapeutic candidates developed via combinatorial chemistry methods, is screened for interactions with a target molecule. Subsequent to this analysis, a second screen is performed for all candidate molecules that were observed to interact with the target molecule using a complementary technique, such as 2D NMR spectroscopic techniques, mass spectrometric methods and surface plasmon resonance techniques.

BRIEF DESCRIPTION OF THE DRAWINGS

FIG. 5A provides an absolute value 2D IR spectrum of 3 M ethyl methylcarbamate and 3M $^{13}$C-urea in dimethylsulphoxide taken with the four beams having the same polarization and using a one-quantum rephasing pulse sequence where the $k_1$ pulse comes before pulses $k_2$ and $k_3$. The peak labeled A at $(\omega_3, -\omega_1)=(1710 \text{ cm}^{-1}, 1710 \text{ cm}^{-1})$ is due to the 1710 cm$^{-1}$ ethyl methylcarbamate mode labeled A in FIG. 3. Peak B (1660, 1660) and peak C (1610, 1610) are the $^{13}$C-urea absorptions also seen in FIG. 4. Peak D at (1540, 1540) is the ethyl methylcarbamate mode labeled D in FIG. 3. The "diagonal" features A, B, C and D are the most intense features. The cross peaks are weaker. Representative cross peaks are labeled M and N that appear at approximately (1625, 1710) and (1710, 1610). Peak N is the strongest cross peak and peaks M and N are cross peaks between the $^{13}$C-urea and ethyl methylcarbamate.

FIG. 5B provides an absolute value 2D IR spectrum of 3 M ethyl methylcarbamate and 3M $^{13}$C-urea in dimethylsulphoxide taken with the four beams having the same polarization and using a one-quantum non-rephasing pulse sequence where the $k_2$ pulse comes before pulses $k_1$ and $k_3$. The peak intensities and shapes are different than in FIG. 5A. Some cross peaks are better resolved, for example P. A new cross peaks appear that are labeled O, P, and Q at $(\omega_3, \omega_1)=(1540, 1710), (1710, 1540),$ and $(1600, 1540)$. Peaks O and P are due to coupling between peaks A and D of the ethyl methylcarbamate and peak Q is caused by coupling between the $^{13}$C-urea and ethyl methylcarbamate modes labeled C and D. A cross peak S (1660, 1610) is also now apparent, caused by intramolecular coupling between the urea absorptions B and C.

FIG. 5C provides an absolute value 2D IR spectrum of 3 M ethyl methylcarbamate and 3M $^{13}$C-urea in dimethylsulphoxide taken with the four beams having the polarizations 90°, −45°, +45° and 0° written in the order of $k_2$, $k_1$, $k_3$ and the local oscillator where the spectrum is collected using a one-quantum non-rephasing pulse sequence where the $k_2$ pulse comes before pulses $k_1$ and $k_3$. This polarization condition reduces the contributions from the diagonal peaks A, B, C and D and emphasizes the contributions from cross peaks that are generated from non-parallel transition dipoles. As a result, most cross peaks are much better resolved and much more intense relative to the maximum intensity of the spectrum. Peaks O and P are now more apparent, as are M and N. The most intense features are peaks R (1610, 1660) and S, caused by intramolecular coupling between the B and C $^{13}$C-urea absorptions.

FIG. 5D provides an absolute value 2D IR spectrum of approximately 1M ethyl methylcarbamate and approximately 3M $^{13}$C-urea in dimethylsulphoxide taken with the four beams having the polarizations 90°, −45°, +45° and 0° written in the order of $k_2$, $k_1$, $k_3$ and the local oscillator where the spectrum is collected using a one-quantum non-rephasing pulse sequence where the $k_2$ pulse comes before pulses $k_1$ and $k_3$. The intensities of the ethyl methylcarbamate peaks decrease (A and D) as do cross peaks between the $^{13}$C-urea and ethyl methylcarbamate (M and N, for example).

FIG. 5E provides an absolute value 2D IR spectrum generated by subtracting the complex parts of the data in FIGS. 5A and 5B. This procedure removes the phase twisting effects in the 2D IR spectra to generate absorptive features. Spectra with different beam polarizations and/or different pulse sequences can also be subtracted to enhance, suppress, or eliminate features, as is known to people familiar with the art.

FIG. 10 shows a two dimensional spectrum of a mixture of acetonitrile ($CH_3CN$), deuterated acetonitrile ($CH_3CN$), and deuterated benzene ($C_6D_6$)

DETAILED DESCRIPTION OF THE INVENTION

Figure 1:
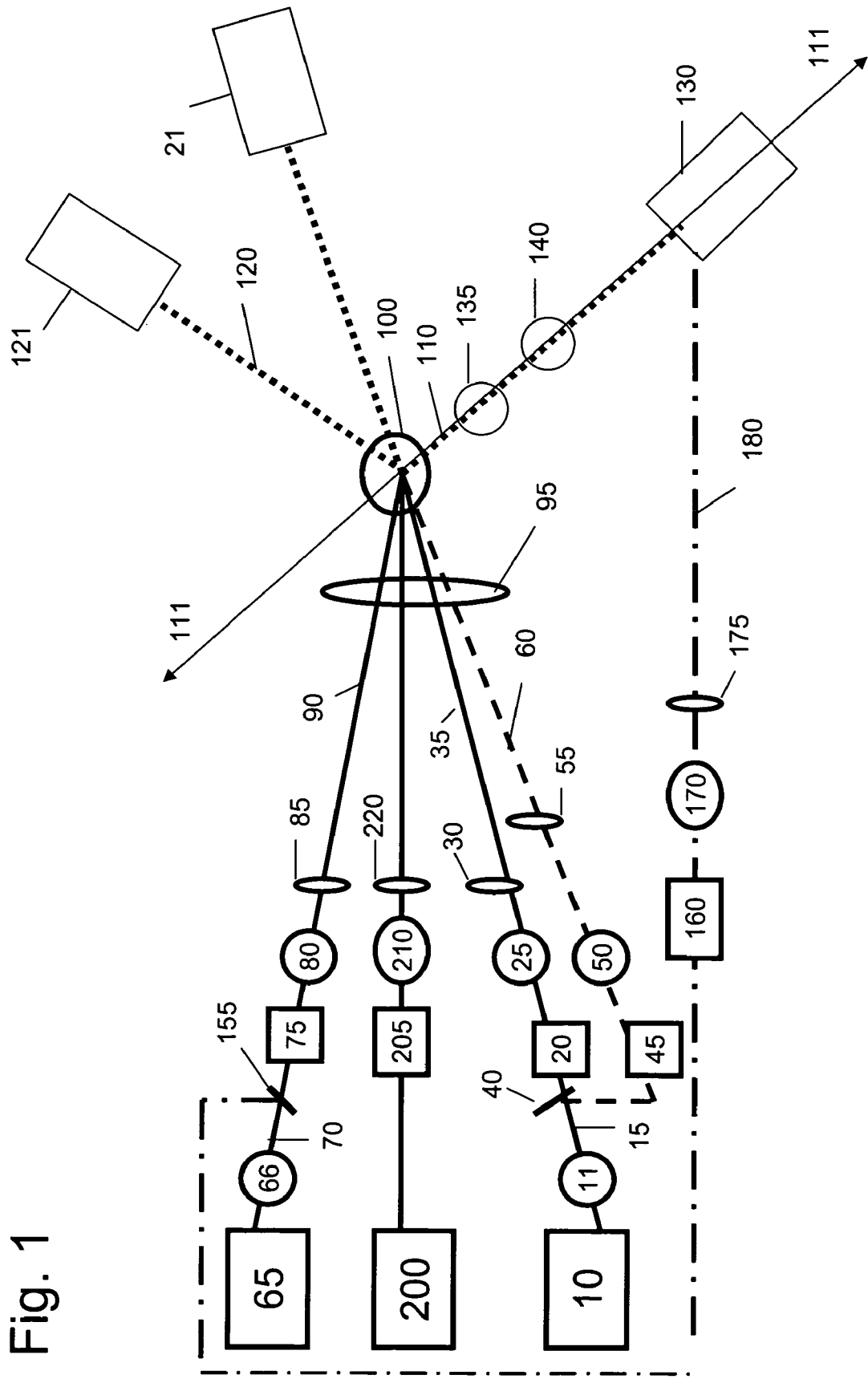
FIG. 1 schematically illustrates exemplary methods and devices using multidimensional vibrational spectroscopy techniques for identifying and/or characterizing interactions involving a target molecule and a candidate molecule.

Referring to the drawings, like numerals indicate like elements and the same number appearing in more than one drawing refers to the same element. In addition, hereinafter, the following definitions apply:

"Multidimensional vibrational spectroscopy" and "multidimensional electronic spectroscopy" refer to coherent nonlinear optical techniques and incoherent analogous for probing intramolecular and/or intermolecular interactions that couple a plurality of resonant vibrational and/or electronic states in one or more molecules, such as target molecules, candidate molecules or both. In these techniques, the vibrational or electronic states in the molecule(s) are probed with electromagnetic radiation to ascertain the anharmonicities of the potential surfaces. Multidimensional vibrational and electronic spectroscopic techniques useful in the present invention include multidimensional IR spectroscopy, multidimensional Raman spectroscopy, multidimensional hyperRaman spectroscopy, multidimensional electronic spectroscopy and any combination of the above. In one embodiment, the methods of the present invention employ 2D IR spectroscopy wherein intramolecular and/or intermolecular processes that couple two vibrational modes are probed. If the two modes are coupled and/or energy transfer and/or population transfer and/or coherence transfer occurs, cross peaks at the frequency of each mode and at other transition frequencies appear in the 2 dimensional spectra obtained using this technique.

"Contacting" refers to a process in which two or more molecules or two or more components of the same molecule or different molecules are brought into physical proximity such that they are able undergo an interaction. Molecules or components thereof may be contacted by combining two or more different components containing molecules, for example by mixing two or more solution components, preparing a solution comprising two or more molecules such as target, candidate or competitive binding reference molecules, and/or combining two or more flowing components. Alternatively, molecules or components thereof may be contacted combining a fluid component with molecules immobilized on or in a substrate, such as a polymer bead, a membrane, a polymeric glass substrate or substrate surface derivatized to provide immobilization of target molecules, candidate molecules, competitive binding reference molecules or any combination of these. Molecules or components thereof may be contacted by selectively adjusting solution conditions such as, the composition of the solution, ion strength, pH or temperature. Molecules or components thereof may be contacted in a static vessel, such as a microwell of a microarray system, or a flow-through system, such as a microfluidic or nanofluidic system. Molecules or components thereof may be contacted in or on a variety of media, including liquids, solutions, colloids, suspensions, emulsions, gels, solids, membrane surfaces, glass surfaces, polymer surfaces, vesicle samples, bilayer samples, micelle samples and other types of cellular models or any combination of these.

The terms "electromagnetic radiation" and "light" are used synonymously in the present application and refer to waves of electric and magnetic fields. Electromagnetic radiation useful for the methods of the present invention includes, but is not limited to, infrared light, ultraviolet light, visible light or any combination of these. The methods and devices of the present invention use coherent electromagnetic radiation which can be characterized in terms of a frequency distribution comprising the distribution of intensities corresponding to a range of frequencies having defined phase relations as a function of time. Coherent electromagnetic radiation useful in the methods of the present invention may have any frequency distribution, temporal profile, and/or phase distribution capable of generating an appropriate signal beam or multidimensional spectrum. Coherent electromagnetic radiation of the present invention may also be characterized in terms of coherence length, spatial coherence, temporal coherence length, bandwidth, center wavelength, frequency distribution, time distribution, phase distribution, spatial profile or any combination of these properties.

"Beam of light", "light beam", "electromagnetic radiation beam" and "beam of electromagnetic radiation" are used synonymously and refer to electromagnetic radiation propagating in the same direction. In the present description, use of the term beam of light is intended to be consistent with use of this term in the art of optics and spectroscopy. Beams of light useful in the methods of the present invention included coherent beams of light, pulses of light and coherent pulses of light. Beams of light useful in some applications comprise photons having substantially parallel propagation axes. In this context the term "parallel" refers to a geometry in which two axes are equidistant from each other at all points and the term "substantially parallel" is intended to refer to a geometry including some deviations from absolute parallelism. Beams of light useful in the present methods may be focusing, diverging, collimated, semicolllimated or noncollimated.

"Pulse of light" and "pulse of electromagnetic radiation" are used synonymously in the present application and refer to a temporally and spatially localized distribution of photons propagating through space. In the present description, use of the term pulse of light is intended to be consistent with use of this term in the art of optics and spectroscopy. Pulses of light may be characterized in terms of the time-dependence of the electromagnetic field comprising the pulse as a function of time as the pulse pass through a plane positioned orthogonal to the propagation axes of the pulse. Pulses of light useful in the methods of the present invention may have any temporal profile, such as a temporal profile having a plurality of maxima. Pulses of light useable in the present invention can comprised of one or more subpulses that are separated in time or overlap in time. The present invention includes methods wherein the temporal profile of one or more pulse of light delivered to a sample is selected, selectively adjusted or tuned using a beam shaping device such as a liquid crystal modulator or a acousto-optic modulator. Devices that utilize, but are not limited to, holographic gratings, cube polarizers, beam splitters and diffractive optics are also included in this invention.

The terms "interaction" and "coupling" refers to physical and/or electrostatic processes involving one or more moieties that have a measurable effect on the quantum states, such as vibrational states and/or electronic states, of at least one molecule participating in an interaction. In the context of this description, the term "moiety" is used broadly to refer to a component part of a molecule, such as an atom, a group of atoms or a structural domain of a molecule. Interactions may involve moieties from two or more molecules or between two or more moieties within a single molecule. Interactions having a measurable effect on the quantum states of a molecule participating in an interaction can be interactions that affect the structure or composition of one or more molecule(s) participating in an interaction. In one aspect of the present invention, the term "interaction" refers to a measurable chemical or physical interaction between a target molecule and a candidate molecule that is capable of affecting the structure and/or composition of a target molecule, a candidate molecule or both such that the biological activity of the target molecule, the candidate molecule or both is affected. Interactions capable of affecting the structure and/or composition of a molecule include, but are not limited to, reactions resulting in the formation of one or more covalent bonds, resulting in the breaking of one or more covalent bonds, electrostatic associations and repulsions, formation and/or disruption of hydrogen bonds, formation and/or disruption of electrostatic forces such as dipole-dipole interactions, formation and/or disruption of van der Waals interactions or processes comprising combinations of these. The present methods are capable of identifying and/or characterizing interactions of a candidate molecule that inhibits the biological activity of the target molecule, decreases the biological activity of the target molecule or enhances the biological activity of the target molecule. The present methods are useful for identifying and/or characterizing associative interactions between a target molecule and a candidate molecule, such as an associative interaction of a therapeutic candidate and a biomolecule, which results in formation of a molecular complex. Associative interactions in the present invention includes the association of a single candidate molecule and a single target molecule, and also includes association of a plurality of candidate molecules and one or more target molecules. In addition, the present methods are useful for identifying and/or characterizing non-associative interactions between a target molecule and a candidate molecule that result in a change in the composition and/or structure of the candidate molecule, target molecule or both, such as post-translational or co-translational processes, enzymatic reactions or molecular complex formation reactions involving one or more proteins.

"Molecule" refers to a collection of chemically bound atoms with a characteristic composition. As used herein, a molecule can be neutral or can be electrically charged. The term molecule includes biomolecules, which are molecules that are produced by an organism or are important to a living organism, including, but not limited to, proteins, peptides, lipids, DNA molecules, RNA molecules, oligonucleotides, carbohydrates, polysaccharides; glycoproteins, lipoproteins, sugars and derivatives, variants and complexes of these, including labeled analogs of these having one or more vibrational tag. The term molecule also includes candidate molecules, which comprise any molecule that it is useful, beneficial or desirable to probe its capable to interact with a molecule such as a target molecule. Candidate molecules include therapeutic candidate molecules which are molecules that may have some effect on a biological process or series of biological processes when administered. Therapeutic candidate molecules include, but are not limited to, drugs, pharmaceuticals, potential drug candidates and metabolites of drugs, biological therapeutics, potential biological therapeutic candidates and metabolites of biological therapeutics, organic, inorganic and/or hybrid organic-inorganic molecules that interact with one or more biomolecules, molecules that inhibit, decrease or increase the bioactivity of a biomolecule, inhibitors, ligands and derivatives, variants and complexes of these, including labeled analogs of these having one or more vibrational tag. The term molecule also includes target molecules, which comprise any molecule that is useful, beneficial or desirable to probe its capable to interact with a molecule such as a candidate molecule. Target molecules useful for identifying, characterizing and/or optimizing therapeutics and therapeutic candidates comprise biomolecules, and derivatives, variants and complexes of biomolecules, including labeled analogs of these having one or more vibrational tag. The term molecule also includes competitive binding reference molecules. Competitive binding reference molecules useful in the present invention are molecules that are known to bind, at least to some extent, to a target molecule, and in some embodiments comprise a known drug, biological therapeutic, biomolecule, lead compound in a drug discovery program, and derivatives, variants, metabolites and complexes of these, including labeled analogs of these having one or more vibrational tag.

"Vibrational tag" refers to a spectroscopic label useful for introducing radiant energy into a molecule in a concerted manner and/or useful for detecting interactions between molecules such as an interaction between a target molecule and a candidate molecule. In one embodiment, vibrational tags are incorporated into a molecule to be labeled and provide for at least one additional vibrational mode having a selected resonance frequency, such as a resonance frequency that is selected so as not to overlap substantially with other vibrational modes of the molecule labeled with a vibrational tag. In one embodiment, a vibration tag refers to atoms and/or groups of atoms that are added to the molecule, such as atoms or groups of atoms that are covalently bound to or electrostatically incorporated into the molecule, that affect the absorption of light by the molecule, such as absorption of light in the infrared, visible and ultraviolet regions of the electromagnetic spectrum. Exemplary atoms and groups of atoms providing useful vibrational tags for proteins and peptides, such as proteins and/or peptides providing target molecules and/or candidate molecules in the present methods, have resonance frequencies selected over the range of about 1900 cm$^{-1}$ to about 2300 cm$^{-1}$ and include, but are not limited to, a azido groups (—N=N=N$^-$), aliphatic diazo groups (C=N=N), cyano groups (—C≡N), cynate groups, (—N=C=O), thiocynates (—N=C=S; —S—C≡N), ketene groups (C=O=O), isocyanate groups (—N=C=O), isothiocyanate groups (—N=C=S), aminonitriles (N—C≡N), isonitrile groups (—N≡C), carbonyl groups (—C=O), mono-substituted acetylene groups (—C≡C—H), di-substituted acetylene groups (—C≡C—), nitrile groups (—CH$_2$—C≡N), acrylonitriles (—C+C—C≡N) or any combination of these. Other exemplary atoms and groups of atoms providing useful vibrational tags have resonance frequencies selected over the range of about 1000 cm$^{-1}$ to about 1300 cm$^{-1}$ and include, but are not limited to S=O, P=O, and C=S. Exemplary atoms and groups of atoms also providing useful vibrational tags in the present invention may also comprise groups having one or more stable isotopes exhibiting a significant shift in resonance frequency relative to the resonance frequency of other more common isotopes, such as groups having one or more C—$^2$H or C—$^2$H bond, one or more C=$^{34}$S bonds, one or more C=$^{18}$O bonds, C=$^{17}$O bonds, groups having a $^{13}$C or combinations of these. Candidate molecules, target molecules and/or competitive binding reference molecules having a vibrational tag may also comprise a sample containing at least on of these materials that is enriched with a selected stable isotope, such as deuterium or sulfur-34 ($^{34}$S).

In the following description, numerous specific details of the devices, device components and methods of the present invention are set forth in order to provide a thorough explanation of the precise nature of the invention. It will be apparent, however, to those of skill in the art that the invention can be practiced without these specific details.

This invention provides methods and devices for identifying and/or characterizing interactions involving molecules, such as target molecules and candidate molecules. Particularly, the present invention provides methods of using multi-dimensional infrared spectrographic techniques, such as four wave mixing and pump-probe techniques, for identifying and/or characterizing interactions involving biomolecules and therapeutic candidate molecules that may serve the basis of a new or improved therapy.

In multidimensional infrared techniques, a sample is illuminated with one or more coherent pulses of electromagnetic radiation and signal beams are either collected in the time-domain by varying the relative delays between a sequence of short pulses or in the frequency domain by scanning the wavelengths of narrow band laser beams. In some of these techniques, measurement of the time dependent signal (i.e. intensity or amplitude of the electric field) corresponding to the signal beam may be used to generate a multidimensional dimensional infrared spectrum, which contains information about the structures of molecules in the sample. The dimensionality of the spectrum is determined by the number of time-delays or frequencies varied in the experiment and the possible number of multidimensional spectra grows with the number of pulses employed. In third-order spectroscopy, for example, 2D and 3D experiments are possible since three laser pulses are used to interrogate the sample. Choosing which combination of pulse delays or frequencies to vary depends on the desired information and an understanding of the couplings and dynamics inherent to the system. For example, peaks can be suppressed or narrowed using appropriate time-delays, pulse sequences, phases, polarizations and phase matching directions.

Non-linear infrared spectroscopy techniques useful in the present invention include third-order spectroscopic techniques, wherein the order refers to the number of times the sample interacts with the incident electromagnetic fields. Third-order techniques include pump-probe and photon echo spectroscopies and are often referred to as four-wave mixing techniques. All of these third-order techniques can be carried out in such a way as to generate 2D and 3D multidimensional spectra useful in the methods of the present invention. The differences in the various four-wave mixing techniques lies in the number of pulses used, as well as their temporal, spatial, and wavelength distributions.

For example, in pump-probe spectroscopy, two pulses are used; the pump pulse and a weaker probe pulse. The pump pulse excites the sample, and the probe pulse interrogates the effects of the pump. One way of generating a 2D IR spectrum from a pump-probe spectrum, is to use a narrow band pump pulse that excites a small distribution of vibrational modes and a broad band probe pulse to measure the effect of the pump pulse on a large distribution of vibrational modes. The frequency of the pump pulse is scanned across the desired frequency range. By subtracting the spectrum of the probe pulse with and without the pump pulse interacting with the sample, a difference spectrum is obtained that has diagonal pairs of peaks for each fundamental frequency being probed and cross peaks between coupled modes. In the weak coupling limit, when the oscillators retain their primary vibrational characteristics, the diagonal pairs of peaks consist of one peak due to pulses accessing the ground and first excited (i.e. fundamental) states and a second peak for pulses that access the second excited (i.e. overtone) state. The off-diagonal pair of cross peaks has one peak arising from pulses that access both the first excited states of two vibrational modes and a second peak from pulses that access the combination band. When there is no interaction between the two vibrational modes, these two peaks exactly cancel one another. Coupling between the modes creates off-diagonal anharmonicity that separates the frequencies of the two cross peaks so that they do not cancel. In the present methods, however, an entire spectrum does not need to be obtained to ascertain whether there is coupling between two vibrational modes, because the pump can be tuned to excited one mode of interest while the probe monitors the second mode.

A simple variation on a pump-probe experiment is a two-pulse photon echo method. This variation again uses two pulses, but instead of monitoring the signal in the direction of the probe pulse, the signal is monitored in the $k_s = -k_1 + 2k_2$ phase matching direction where $k_1$ is the wavevector of one pulse and $k_2$ is the wavevector of the second pulse. The signal is emitted primarily in the ks phase matching direction, although it radiates in other directions as well and is quantitatively described by Maxwell's equations. To collect a full 2D IR spectrum, the emitted electric field is heterodyned, and the signal is collected as a function of time between k1 and k2 and as a function of time between k2 and the heterodyned beam. Like pump-probe spectroscopy, the two-pulse photon echo is also a four-wave mixing or third-order spectrum, but it has additional advantages. One advantage is that since the second pulse itself is not measured, it can be as intense as the pump pulse, and thus a larger signal can be obtained. Furthermore, it is a background free technique. That is, a difference spectrum does not need to be measured in order to remove the intensity of the probe pulse. This is particular advantageous for the high-throughput screening methods when one is quickly trying to ascertain the occurrence of an interaction, such as an associative interaction, between target and candidate molecules, because if one pulse is tuned to the candidate molecule and the other to the target, a signal pulse will only appear in the photon echo signal direction if the target and candidate molecules are interacting (i.e vibrational modes are coupled).

A more complicated variant on a pump-probe experiment is a three-pulse photon echo method. In the pump-probe and two-pulse photon echo techniques, one pulse always interacted with the sample twice, whereas in the three-pulse photon echo three spatially separated beams are used that each interact with the sample once. For three beams with wavevectors, $k_1$, $k_2$, and $k_3$, the third-order signals are emitted in the $k_s = -k_1 + k_2 + k_3$, $k_s = k_1 - k_2 + k_3$, and $k_s = k_1 + k_2 - k_3$ phase matching directions, although other direction are also possible as Maxwell's equations describe. Solving Maxwell's equations gives the radiated electric field $$E_s(l, t) = \frac{2\pi i}{n(\omega_s)} \frac{\omega_s}{c} l P_s(t) \frac{\sin(\Delta k l/2)}{\Delta k l/2} \exp(i\, \Delta k l/2)$$

where $n(\omega_s)$ is the frequency dependent index of refraction, $\omega_s$ is the signal frequency, c is the speed of light, l is the sample thickness, $P_s(t)$ is the time-dependent polarization of the sample, $\Delta k$ is the difference between the combination of incoming wavevectors and the wavevector of the generated wave.

The advantage of having three pulses is that the time-delays between them can be set to optimize the signal strength in a particular phase matching direction, discriminate undesired signals by their vibrational dynamics or population relaxation times, and control of the polarization for all three pulse interactions to eliminate undesired peaks or enhance features. Once again, the signal emitted in these three directions are third-order signals.

Signal pulses generated in these coherent nonlinear techniques can be analyzed in a variety of ways including, but not limited to, time-resolved with heterodyning or balance heterodyning or time-gating with up-conversion; frequency resolved with a spectrometer; or any combinations of these. The techniques can be used with either broad bandwidth pulses to excite a large number of resonances simultaneously or narrow bandwidth pulses to selectively interrogate specific modes. Furthermore, the methods of the present invention are not limited to third-order techniques. For example, $5^{th}$-order, $7^{th}$-order, and higher order techniques can also be used to probe interactions between molecules or interactions within molecules. This can be accomplished, for example, by adding additional pulses with additional time-delays or by looking in new phase matching directions that require additional pulse interactions, or both. For example, one of many possible $5^{th}$-order signals is generated most strongly in the $k_s=-k_1-k_2+k_3+k_4+k_5$ for five pulses that each interact with the sample once, and in the $k_s=-2k_1+k_2+2k_3$ phase matching direction for three pulses where the first and $3^{rd}$ pulses interact twice. The signal that results from nth-order spectroscopies can be described by a perturbative expansion of the density matrix, which is often described by double sided Feynman diagrams. The perturbative description is best used when the pulse intensities are weak and the coherence or population state created by the pulses is only a few percent of the available molecules (hence a perturbative interaction). For strong pulses, as determined when the Rabi Frequency becomes short enough for substantial (>10%) excitation, the perturbative approach is not appropriate because many higher-order interactions occur which will contribute to the lower-order signals in the lower-order signal phase matching directions. The simplest example of this, is overpumping in a pump-probe or photon echo signal, when one pulse interacts an additional two times, creating transitions up to the third-excited state. Pulse shaping techniques also rely on interfering multiple pathways and signals of different orders and thus are also not well-described by the traditional perturbative approach. When a perturabative approach is not sufficient, the density matrix must be propogated exactly and the techniques cannot be classified as nth-order. Nonetheless, 2D, 3D, and nD spectroscopies can be based on nth-order spectroscopies, with pulse delays, polarizations, and frequencies optimized for the target/candidate systems of interest.

FIG. 1 schematically illustrates exemplary methods and devices using multidimensional infrared techniques for identifying and/or characterizing an interaction involving a target molecule and a candidate molecule. The methods and devices represented in FIG. 1 are particularly well suited for high-throughput applications for screening a plurality of candidate molecules for the occurrence of interactions or absence of interactions with a target molecule, such as a protein or peptide, and for structure based approaches for characterizing the location and structure of binding region(s), binding affinity and dissociation constant corresponding to an interaction between a target molecule and a candidate molecule. As shown in FIG. 1, an optical source 10 is provided for generating coherent light 15, for example a laser pulse of coherent infrared light or a laser pulse of coherent near-infrared light such as from a Ti:Sapphire based laser. The laser may use be tunable or have a fixed frequency. Optionally, optical source 10 may be coupled to an optical parametric amplifier or other non-linear device 11 to generate a specific time and frequency distribution of coherent electromagnetic radiation. Optical parametric amplifier or other non-linear device 11 may be an integrated component of optical source 10 or may be a separate optical component in optical communication with optical source 10. At least a portion of coherent light 15 passes through a first delay stage 20, a first wavelength selection and/or temporal profile selection device 25, such as a filter or liquid crystal modulator, and a first polarization state adjustor 30, such as a waveplate and/or polarizer, thereby generating a first coherent excitation pulse of electromagnetic radiation 35, for example a femtosecond IR pulse. Optionally, coherent light 15 interacts with a beam splitting device 40, thereby generating coherent light that passes through a second delay stage 45, a second wavelength selection and/or temporal profile selection device 50, such as a filter or liquid crystal modulator, and a second polarization state adjustor 55, such as a waveplate and/or polarizer, thereby generating a second coherent excitation pulse of electromagnetic radiation 60, for example a femtosecond IR pulse.

As shown in FIG. 1, optical source 65 is optionally provided for generating coherent light 70 for example a laser pulse of coherent infrared light. Optical source 65 provides coherent light that is either phase locked to the coherent light of 10 or not phase locked to the coherent light of 10. Optionally, optical source 65 may be coupled to an optical parametric amplifier or other non-linear device 66 to generate a specific time and frequency distribution of coherent electromagnetic radiation. Optical parametric amplifier or other non-linear device 66 may be an integrated component of optical source 10 or may be a separate optical component in optical communication with optical source 10. At least a portion of coherent light 70 passes through a third delay stage 75, a first wavelength selection and/or temporal profile selection device 80, such as a filter or liquid crystal modulator, and a third polarization state adjustor 85, such as a waveplate and/or polarizer, thereby generating a third coherent excitation pulse of electromagnetic radiation 90, for example a femtosecond IR pulse.

In one embodiment, first coherent excitation pulse 35 has a first selected wavelength distribution, second coherent excitation pulse 60 has a second selected wavelength distribution and third coherent excitation pulse 90 has a third selected wavelength distribution. First, second, and third wavelength distributions can be the same or different. In an embodiment useful for some high-throughput applications first and second distributions of first and second coherent excitation pulses 35 and 60 are substantially identical, and third wavelength distribution of third coherent excitation pulse 90 is different from first and second distributions. As will be understood by persons skilled in the art, first, second, and third wavelength distributions can be maintained at selected distributions or selectively adjusted (i.e. tuned).

First coherent excitation pulse 35, second coherent excitation pulse 60 and optionally third coherent excitation pulse 90 are provided to a focusing element 95, such as a lens or focusing reflector, and are focused onto a sample 100 containing a target molecule, candidate molecule or both. In one embodiment, first, second and third delay stages provide first, second and third coherent excitation pulses 35, 60 and 90 which are delivered to sample at different times. For example, first, second and third delay stages may provide first, second and third coherent excitation pulses 35, 60 and 90 in any order using selected delay times between excitation pulses. In one embodiment, first coherent excitation pulse 35 is provide to the sample 100 at a first time, and is followed by third coherent excitation pulse 90 at a second time a selected first delay time after the first time of the first coherent excitation pulse 35. Second coherent excitation pulse 60 is provided to the sample 100 next at a second delay time after the first time of the first coherent excitation pulse 35, wherein the second delay time is greater than the first delay time. The present invention includes embodiments wherein delay times between coherent excitation pulses are computer controlled and are capable of providing first, second and optionally third excitation pulses to sample 100 in any sequence and using any relative temporal configuration of excitation pulses.

First coherent excitation pulse 35, second coherent excitation pulse 60 and optionally third coherent excitation pulse 90 coherently excite selected vibrational modes in a target molecule, candidate molecule or both in sample 100, after which the sample radiates generating at least one signal beam 110. In one embodiment of the present invention shown in FIG. 1, the signal beam 110 propagates parallel to a detection axis 111 that is spatially separated from the propagation axes first coherent excitation pulse 35, second coherent excitation pulse and 60 third coherent excitation pulse 90. In an embodiment, for example, signal beam 110 results from the interaction of the first coherent excitation pulse 35, the second coherent excitation pulse 60, optionally the third coherent excitation pulse 90 or any combination of these with an induced refractive index formed by optical interference of the first coherent excitation pulse 35, the second coherent excitation pulse 60, optionally the third coherent excitation pulse 90 or any combination of these, commonly called phase matching. As also shown in FIG. 1, coherent excitation of sample 100 may also generate one or more additional signal beams 120, which can also propagate along axes that are parallel to additional detection axes that are spatially separated from the propagation axes first coherent excitation pulse 35, second coherent excitation pulse and 60 third coherent excitation pulse 90. Alternatively, coherent excitation of sample 100 can also generate a signal beam 122 that propagates along an optical axis coincident with the propagation axis of first excitation pulse 35, second excitation pulse 60 or third excitation pulse 90 (solely for the sake of clarity signal beam 122 is shown propagating along a axis coincident with the optical axis of first excitation pulse 35 although other configurations are included in the present invention).

Signal beam 110 is provided to detector 130, such as an infrared light detector, wherein the intensity, amplitude of the electric field, and/or polarization state is detected. Optionally, signal beam 119 is provided to a wavelength selection device 135 and/or polarization adjustor 140 prior to detection by detector 130. Detector 130 may be configured in a gated detection mode wherein signal (e.g. intensity) of the signal beam 110 is detected and integrated over a preselected time interval beginning at detection time after a preselected detection delay time from the first time of the first coherent excitation pulse 35. Alternatively, detector 130 may be configured in a continuous detection mode capable of measuring the time-dependent signal (e.g. intensity) of the signal beam 110 is detected. In some embodiments, one or more additional detectors 121 are provided to detect additional signal beams generated by coherent excitation of the sample.

Alternatively, detector 130 can be configured in a heterodyned detection mode to provide measurements of the amplitude and/or time-dependence of the electric field of the signal beam 110. In one embodiment, a portion of coherent light 70 interacts with a beam splitting device 155, thereby generating coherent light that passes through a fourth delay stage 160, a fourth wavelength selection and/or temporal profile selection device 170, such as an optical parametric amplifier, and a fourth polarization state adjustor 175, such as a waveplate and/or polarizer, thereby generating a heterodyned detection pulse of electromagnetic radiation 180, for example a femtosecond IR pulse. Heterodyned detection pulse of electromagnetic radiation 180 is directed to detector 130 and detected. Fourth delay stage 160 provides heterodyned detection pulse 180 to detector 130 at a time substantially equivalent to the time that signal beam 110 is provided to detector 130, thereby allowing measurement of the amplitude of the electric field of signal beam 110.

Referring again to FIG. 1, the present invention includes methods and devices wherein one or more addition optical sources 200, delay stages 205, wavelength selection and/or temporal profile selection devices 210 and polarization adjustors 220 are provided to generate additional coherent pulses of electromagnetic radiation that are focused onto sample 100, and which can be phase locked to the other optical sources or coherent optical beams 90, 25, and 60 or not phase locked to the other optical sources or coherent optical beams 90, 25, and 60. Embodiments of these aspects of the present invention are useful for providing higher order multidimensional IR spectroscopic techniques and/or for providing background subtraction and/or for triggering chemical events such as a photodissociation, temperature jump, electron transfer event, enzymatic reaction or other light-driven chemical or biological process. Furthermore, optical source 200 or additional optical sources or beams can be used in coincidence or near coincidence to simultaneously or near simultaneously measure the signal of the candidate molecule, target molecule, or both. This second signal could be subtracted or compared to the first signal to determine whether a binding event changed the multidimensional spectrum. This embodiment of the present invention provides an apparatus capable of analyzing a plurality of difference samples simultaneously or nearly simultaneously, such as different samples corresponding to a target molecule, a candidate molecule and a mixture comprising the target molecule and the candidate molecule. An advantage of this embodiment is that all three signals necessary to determine if an interaction between target and candidate occurs can be compared and analyzed in tandem, thereby accounting for possible changes in the background signal and any minimizing the occurrence of false positives.

Multiple embodiments of this aspect of the present invention are useful in high throughput screening applications, wherein the presence or absence of an interaction between candidate molecule and target molecule is able to be assessed very rapidly. In the present invention, the rate of determining the presence or absence of an interaction is set by the repetition rates of the optical sources providing coherent excitation pulses, such as IR lasers. In one embodiment, the presence or absence of an interaction between target and candidate molecules may be assessed on a time scale ranging from about 10 s of microsecond to about 10 s of milliseconds. In one embodiment, the wavelength distributions of first, second and optionally third coherent excitation pulses 35, 60 and 90, the delay times between first, second and optionally third coherent excitation pulses 35, 60 and 90, polarization states of first, second and optionally third coherent excitation pulses 35, 60 and 90 or any combination of these parameters are selected such that a signal beam 110 is generated propagating along detection axis 111 only if an interaction occurs between a target molecule and a candidate molecule present in sample 100, such as an associative interaction between target molecule and candidate molecule resulting in formation of a molecular complex having vibrational energy levels and vibrational dynamic processes.

Selection of appropriate wavelength distributions, the delay times and polarization states for this aspect of the present invention are made on the basis of the infrared spectrum frequencies of the target and candidate molecules, secondary and tertiary structures of the molecules, molecular class of target and candidate molecules, vibrational lifetimes, vibrational linewidths, strengths of transition dipoles, relative angles of transition dipoles, nature of target/candidate interaction, correlation in frequency distributions, sample concentration, sample thickness, and solvent identity.

As an example, consider experimental conditions useful for probing a possible interaction involving a selected target protein and a selected candidate molecule having a methyl ester group (—OCH$_3$). In one embodiment, the frequency distributions of coherent excitation pulses 35 and 60 are selected such that these pulses are absorbed principally, if not exclusively, by the protein. This can be achieved, for example, via excitation of the amide I vibrational mode of the protein backbone by selection of frequencies for coherent excitation pulses 35 and 60 over the range of frequencies of about 1670 cm$^{-1}$ to about 1700 cm$^{-1}$. The frequency distribution of coherent excitation pulse 90 is selected such that the pulse is absorbed principally, if not exclusively, by the methyl ester moiety of the candidate molecule by selection of frequencies for coherent excitation pulse 90 over the range of about 1700 cm$^{-1}$ to about 1730 cm$^{-1}$. Alternatively, the target protein may be provided with a vibrational tag having a vibrational mode with resonance frequency that is separated in frequency space from the resonance frequencies of the methyl ester group. For example, a target protein having an azido group can be provided and excited by selection of coherent excitation pulses 35 and 60 having frequencies selected over the range of about 2170 cm$^{-1}$ to about 2080 cm$^{-1}$.

Detector 130 is positioned to detect signal beam 110 along axis 111 corresponding to one of the phase matching directions set by the propagation axes of coherent excitation pulses 35, 60, and 90 and their respective wavelength distributions. If a signal is measured (i.e intensity or amplitude of electric field of signal beam 110), then it is ascertained that the methyl ester group is coupled is some manner to the protein target backbone or other resonance within the bandwidth of coherent excitation pulses 35 and 60. If signal is not measured, then it is ascertained that the candidate is not interacting with the target protein, is not interacting strongly enough to be measured, or is not interacting with the target protein backbone. Optionally, heterodyned detection pulse 180 can be used to increase the signal strength, or alternatively detector 130 can be configured in a balanced heterodyne detection setup or spectrally dispersed as well as numerous other possibilities mentioned above. Optionally, coherent excitation pulses 35 and 60 can be tuned to other resonances of the protein, for example the amide 11 band or resonances of the side chains or resonances associated with the binding site of the candidate molecule, and the process repeated. Likewise, the frequency of coherent excitation pulse 90 can be tuned to another resonance of the candidate molecule and the process repeated. These variations provide a means of probing a wide variety of target molecule and candidate molecule interactions. Furthermore, the polarizations of the coherent excitation pulses and the polarization of the measured signal can be changed or signal collected with two different polarizations and/or two different pulse sequences and added or subtracted. In addition, the temporal profiles, intensities, pulse delays, solvent, concentrations and other parameters of the coherent excitation pulses can be adjusted to enhance the signal beam generated.

In another embodiment useful for high-throughput screening methods, the wavelength distributions of first, second and optionally third coherent excitation pulses 35, 60 and 90, the delay times between first, second and optionally third coherent excitation pulses 35, 60 and 90, polarization states of first, second and optionally third coherent excitation pulses 35, 60 and 90 or any combination of these parameters are selected such that a signal beam 110 is generated for a sample comprising the target molecule in the absence of a candidate molecule. In this embodiment, the intensity and/or amplitude of the electric field of a signal beam 110 is measured under experimental conditions corresponding to the target molecule in the absence of the candidate molecule and/or the candidate molecule in the absence of the target molecule. Next, the target molecule is brought into contact with the candidate molecule and the intensity and/or amplitude of the electric field of a signal beam 110 is measured under experimental conditions corresponding to the target molecule in the presence of the candidate molecule. Measurable differences in the intensity and/or amplitude of the electric field of signal beams 110 corresponding to the presence and absence of the candidate molecule or presence and absence of the target molecule, or a comparison of all three signal beams, provide an indication that target and candidate molecules interact, for example interacting in a manner forming a molecular complex. In one embodiment, the target molecule in the absence of the candidate molecule and/or the candidate molecule in the absence of the target molecule is measured simultaneously or near-simultaneously as the sample containing both candidate and target molecules using a second laser device, by using the current laser device to interrogate multiple samples at once or beforehand or afterwards. Selection of appropriate wavelength distributions, the delay times and polarization states for this aspect of the present invention are made on the basis of the infrared spectrum frequencies, secondary and tertiary structures of the molecules, molecular class of target and candidate molecules, vibrational lifetimes, vibrational linewidths, strengths of transition dipoles, relative angles of transition dipoles, nature of target/candidate interaction, correlation in frequency distributions, sample concentration, sample thickness, and solvent.

High-throughput applications of the present methods may by carried out in a scanning mode, wherein a series coherent excitation pulse are provided to individual reaction vessels, such as microwells in a microarray apparatus, in a systematic and sequential manner. In this embodiment, coherent excitation pulses are translated relative to the reaction vessels, the reaction vessels are translated relative to the coherent excitation pulses or a combination of these motions are employed. Alternatively, the present invention provides parallel spectral analysis methods applicable to high-throughput embodiments, wherein a series coherent excitation pulse are simultaneously provided to individual reaction vessels, such as microwells in a microarray apparatus. Exemplary embodiments of this aspect of the present invention may employ one or more diffractive optical elements, multiple lasers, or beam splitters capable of splitting excitation pulses into a plurality of distinct optical beams propagation along different optical axes. Alternatively, the present methods and devices may be incorporated into a flowing system for delivering samples containing target molecules, candidate molecules, competitive binding molecules or mixtures of these to a transparent optical probe region. In one embodiment, a microfluidic or nanofluidic system is provided that is capable of delivering fluid samples to an optical probe region in a microchannel or nanochannel for multidimensional IR spectroscopic analysis. A benefit of the present invention is that the small beam sizes (e.g. spot size as little as 10 microns in diameter) used in coherent excitation pulses enable easy incorporation into and interfacing with microfluidic and nanofluidic systems Multiple embodiments of this aspect of the present invention are useful in structure based drug design and optimization applications. For example, the present invention provides methods for determining the location, structure and conformational changes of binding region(s) for an associative interaction between a target molecule and a candidate molecule. These methods also provide a means of determining the structure of a molecular complex formed by the association of a target molecule and a candidate molecule. In one embodiment, a first 2D IR spectrum is measured for experimental conditions corresponding to the target molecule in the absence of a candidate molecule and a second 2D IR spectrum is measured for experimental conditions corresponding to the target molecule in the presence of a candidate molecule. 2D IR spectra can be measured by monitoring the temporal behavior of one or more signal beams generated by varying the wavelength distributions of first, second and optionally third coherent excitation pulses 35, 60 and 90, the delay times between first, second and optionally third coherent excitation pulses 35, 60 and 90, polarization states of first, second and optionally third coherent excitation pulses 35, 60 and 90 or any combination of these parameters. Differences in first and second 2D IR spectra, such as shifts in the positions and intensity distributions of cross peaks and the appearance of new cross peaks, provide information relating to changes in the atomic scale positions and motions of atoms in the target molecule, for example changes in positions and motions due to the formation of a molecular complex. These differences can be quantified in terms of a difference 2D IR spectrum generated by subtracting the second 2D IR spectrum from the first 2D IR spectrum, which can be numerically simulated to provide structural information relating to the location of bind regions and conformation changes in the target molecule as a result of formation of a molecular complex with the candidate molecule. Numerical simulations also provides structural information relating to how one or more candidate molecules are oriented about the target molecule. Isotope labeling, vibrational tags, and chemical substitutions aid in ascertaining the structural information.

In one embodiment, once an associative interaction between target molecule and candidate molecule is identified, the three-dimensional structure of the resulting molecular complex is determined. Three dimensional structures may be determined by analysis of the 2D IR spectrum corresponding to the target molecule in the presence of the candidate molecule. Alternatively other complementary methods may be employed for determining the structures of a target-candidate molecular complexes, such as NMR and X-ray crystallography methods.

In another embodiment, the present invention provides methods for determining the binding affinity, dissociation constant and/or equilibrium constant for an associative interaction between a target molecule and a candidate molecule. In this aspect, a plurality of 2D IR spectra are measured corresponding to sample conditions of a target molecule in the presence of different concentrations of a candidate molecule. The 2D IR spectrum corresponding to each candidate molecule concentration is subtracted from a 2D IR spectrum corresponding to the target molecule in the absence of target molecule. Differences corresponding to specific frequency combinations (i.e. specific positions in frequency space on the 2D IR spectra) are then analyzed as a function of the concentration of candidate molecule to determine the binding affinity, dissociation constant and/or equilibrium constant. Alternatively, the present invention includes methods, such as those using photon echo techniques, wherein the intensity or amplitude of the electric field of the signal beam is monitored as a function of candidate molecule concentration. In these embodiments, the functional relationship between the intensity or amplitude of the electric field of the signal beam and the concentration of candidate molecule is analyzed to determine the binding affinity, dissociation constant and/or equilibrium constant. In one embodiment of the present invention, the dissociation constant ($K_d$) for an interaction between a target molecule and a candidate molecule is determined using the expression:

$$K_d = \left( \frac{([\text{Target}]_0 - (z)\Delta I)([\text{Candidate}]_0 - (z)\Delta I)}{(z)\Delta I} \right)$$

where $[\text{Target}]_o$ is the initial concentration of the target molecule, $\Delta I$ is the change in intensity of the signal beam ($I_2 - I_1$), $[\text{Candidate}]_o$ is the initial concentration of the candidate molecule and z is a proportionality constant. This expression assumes that the change in the intensity of the signal ($\Delta I$) is linearly proportional to the concentration of the product formed in an association reaction having a one target molecule to one candidate molecule reaction stoichiometry, and assumes experimental conditions are such that equilibrium is reached. This expression may also be used for experiments wherein the amplitude of the electric field of the signal beam is measured by substituting the amplitude of the electric field of the signal beam (E) for the intensity of the signal beam (I) in the expression for $K_d$ provided above.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. Methods and devices useful for the present methods can include a large number of optional device elements and components including, fiber optic elements, birefringent elements such as quarter and half wave plates, optical filters such as FP etalons, high pass cutoff filters and low pass cutoff filters, optical amplifiers, collimation elements such as collimating lens and reflectors, trigger pulse generators, lasers, local oscillators, monochrometers, prisms, diffraction gratings, focusing elements such as focusing lens and reflectors, reflectors, polarizers, fiber optic couplers and transmitters, temperature controllers, temperature sensors, optical parametric amplifier, non-linear crystals, acousto-optic modulators, and broad band optical sources.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation. The scope of the invention shall be limited only by the granted claims.

EXAMPLE 1

Multidimensional IR Spectroscopic Analysis of Peptide-Denaturant Interactions

The ability of the methods and devices of the present invention to detect and characterize interactions involving peptides was verified by experimental studies. Specifically, it is a goal of the present invention to provide multidimensional infrared spectroscopic techniques capable of detecting interactions involving peptides occurring on very short time scales, such as sub-millisecond timescales. Further, it is a goal of the present invention to provide multidimensional infrared spectroscopic techniques capable of characterizing structural changes accompanying an interaction involving peptide.

Figure 2A:
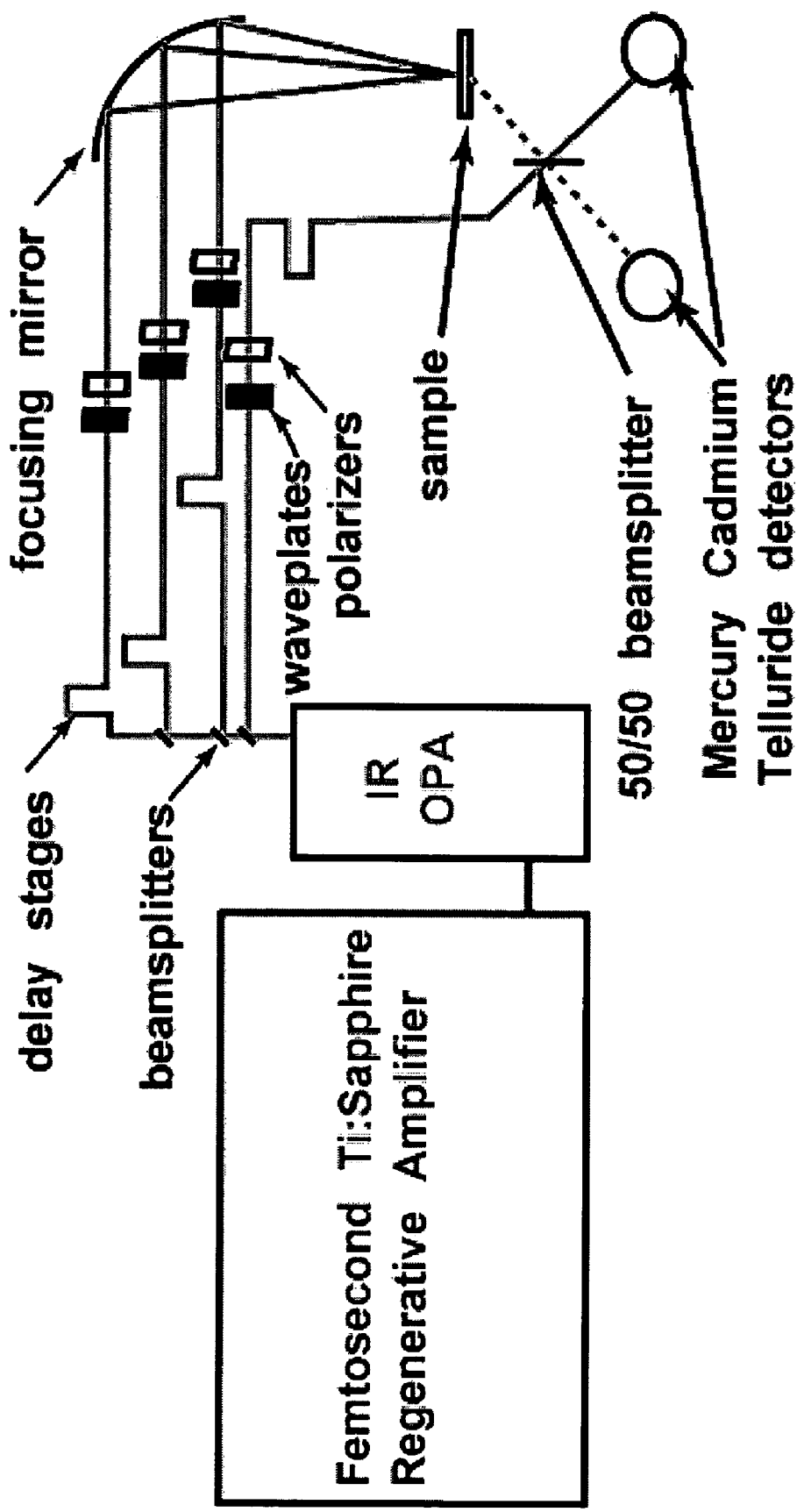
FIG. 2A shows a schematic diagram of the multidimensional vibrational spectroscopic apparatus used to carry out 2D heterodyned photon echo experiments used to generate 2D IR spectra of ethyl methylcarbamate in the presence and absence of urea.
Figure 2C:
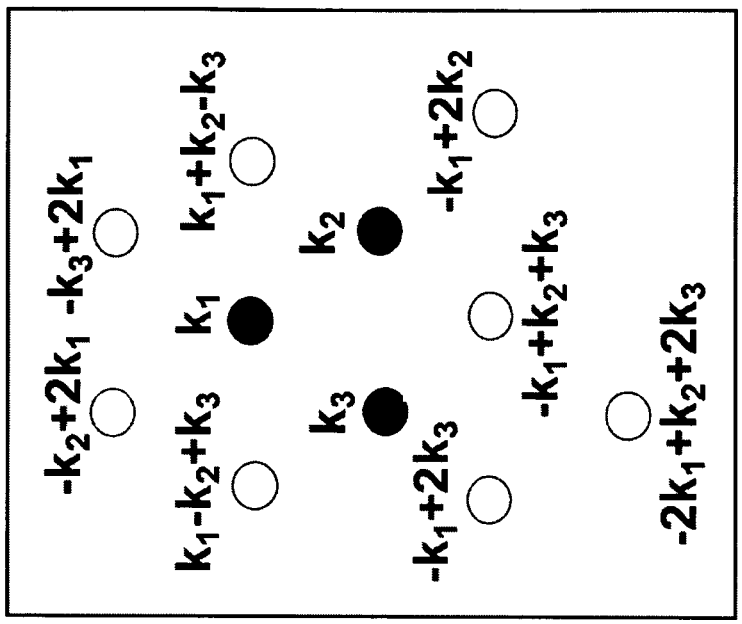
FIG. 2C shows schematic diagram illustrating the position of excitation and signal beams measured by an array detector with signal beam corresponding to $-k_1+k_2+k_3$ and $k_1-k_2+k_3$ wave vector combinations are indicated by arrows.
Figure 2B:
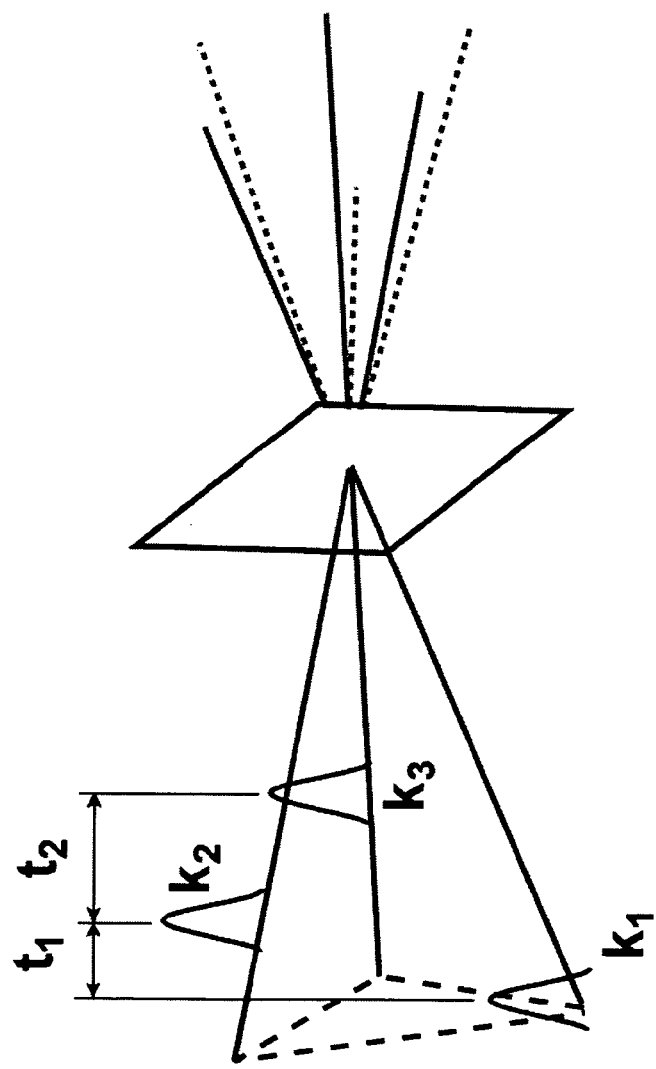
FIG. 2B shows a schematic diagram showing the beam configuration and delay conditions used in these studies.

To achieve the aforementioned goals, two-dimensional IR spectra were measured corresponding to ethyl methylcarbamate in DMSO and various concentrations of the denaturant urea. FIG. 2A shows a schematic diagram of the multidimensional IR spectroscopic apparatus used to carry out 2D heterodyned photon echo experiments used to generate 2D IR spectra of ethyl methylcarbamate in the presence and absence of urea. It consists of a femtosecond Ti:Sapphire laser that pumps an optical parametric amplifier to generate femtosecond pulses of light centered at 1650 cm$^{-1}$. These pulses are split into four beams using dichroic beamsplitters. Three of the beams serve as excitation pulses with wavevectors $k_1$, $k_2$, and $k_3$ that intersect at the sample following delay stages, waveplates, and polarizers to set the delays and polarizations of the three beams. The sample radiates an electromagnetic field that is overlapped with the fourth infrared pulse in the phase matching direction $k_s = -k_1 + k_2 + k_3$ using a 50% reflective/50% transmissive beamsplitter and a balanced heterodyne detection setup with two mercury cadmium telluride (MCT) detectors. FIG. 2B shows a schematic diagram showing the beam configuration and delay conditions used in these studies. The three beams, $k_1$, $k_2$ and $k_3$, interest the sample in an equilateral triangle configuration and are separated in time by $t_1$ and $t_2$. FIG. 2C shows schematic diagram illustrating the position of excitation and signal beams as determined by the excitation beam geometries and phase matching conditions. Signals shown in phase matching directions corresponding to three-pulse echoes ($\pm k_m \pm k_n \pm k_o$, where m, n, and o are integers), two-pulse echoes ($\pm k_m \pm 2k_n$), and one example of a $5^{th}$-order phase matching direction ($-2k_1 + k_2 + 2k_3$). Other phase matching directions exist. For the experiments reported here, the signal was measured in the $-k_1 + k_2 + k_3$ phase matching direction.

The 2D heterodyned photon echo experiments were carried out using a commercial ultrafast amplified Ti:Sapphire laser and a home-built optical parametric amplifier (OPA). The pulses from the Ti:Sapphire are 800 nm with a 90 fs duration at full-width-at-half-maximum (FWHM), and have a repetition rate of 1 kHz. The femtosecond mid-IR pulses are generated in two frequency conversion steps. In the first step, a single-filament white light continuum is used to seed a double-stage BBO (Type II, 4 mm thickness) OPA. The crystal is pumped with ~45 µJ for the first pass and 450 µJ for the second pass, providing an output wavelength tunable between 1.2 and 2.3 µm. Total energy conversions of around 25% are achieved, corresponding to a combined signal and idler energy of 100 µJ. In the second step, the signal and idler are separated using a dichroic mirror, passed through a variable delay line, recombined, and focused into a AgGaS$_2$ crystal (type II, 1.5 mm) for difference frequency mixing. Separating and recombining the signal and idler helps stabilize the mid-IR light. The IR radiation is collimated by a curved mirror and filtered by a Germanium long pass filter. The resulting laser pulses have energies of ~2 µJ and pulse durations of ~120 fs at FWHM.

The mid-IR pulses were tuned to the frequency of the ethyl methylcarbamate and/or $^{13}$C urea absorption bands and split into three equal intensity excitation beams (having wavevectors $k_1$, $k_2$ and $k_3$, ~400 nJ each), and a fourth local oscillator beam (wavevector $k_{LO}$) used in the heterodyned measurements. The pulses will hereafter be referred to by their wavevectors. The $k_1$, $k_3$, and $k_{LO}$ pulses have computer-controlled delay paths, and their time delays are set relative to the $k_2$ pulse. Thus, the order that the pulses $k_1$, $k_2$ and $k_3$ reach the sample can be varied, and the three types of spectra discussed in the Introduction can be measured by changing their relative delays (FIG. 1). For the 1Q rephasing diagrams, the pulse order is $k_1$, $k_2$ and $k_3$, followed by $k_{LO}$; for the 2Q diagrams, it is $k_2$, $k_3$, $k_1$, then $k_{LO}$. The time interval between the first and second pulses is $t_1$, between the second and third is $t_2$, and between the third and $k_{LO}$ is $t_3$.

The three excitation pulses are focused onto the sample with a f=10 cm parabolic mirror in an equilateral triangle configuration, and the time-dependence of the emitted signal, $k_s$, is monitored in the $-k_1 + k_2 + k_3$ phase-matching direction using a balanced heterodyne setup. The emitted field is overlapped with the local oscillator pulse using a 50/50 CaF$_2$ beam splitter, creating two sets of collinear beams propagating in orthogonal directions that are collected on two HgCdTe detectors. The signal on the two detectors is given by, $$S_{\pm}(t_3;t_1,t_2) = \int_{-\infty}^{\infty} dt |E_{gen}(t_1,t_2,t_3) \pm E_{LO}(t-t_3)|^2 = \int_{-\infty}^{\infty} dt \quad (E_{gen}^2 \pm 2E_{gen} \cdot E_{LO} + E_{LO}^2) \quad (1)$$

where $E_{gen}(t_1,t_2,t_3)$ is the emitted field from the sample, $E_{LO}(t-t_3)$ is the local oscillator, and the time notation has been dropped in the final equality. The signals from the two detectors are necessarily out of phase due to conservation of energy, and are subtracted to generate the final signal, $$S(t_3;t_1,t_2) = S_+(t_3;t_1,t_2) - S_-(t_3;t_1,t_2); \quad (2)$$

which removes $E_{gen}^2$ and $E_{LO}^2$. The two signals can either be digitized separately and then subtracted, or first subtracted with an analog circuit and then digitized. In addition, a 500 Hz chopper on the $k_3$ pulse is used to subtract scatter from the $k_1$ and $k_2$ pulses. Using balanced heterodyne detection to remove $E_{gen}^2$ and $E_{LO}^2$ from the signal for each laser shot improves the signal-to-noise over a collinear heterodyne detection system. We have obtained 2-4 fold improvements in signal-to-noise of the 2D IR spectra for various frequency ranges of the spectra, although it is in principle possible to obtain much higher improvements.

Two types of 2D IR spectra were acquired in these experiments, rephasing and non-rephasing spectra. For the rephasing 2D IR experiments (pulse order of $k_1$, $k_2$, $k_3$, and $k_{LO}$), $t_1$ was stepped from 0 to 2200 fs in 4 fs steps by moving $k_1$, and for each $t_1$ delay, the heterodyned signal was recorded for $t_3$ stepped from 0 to 2400 fs in 14 fs steps by moving $k_{LO}$. For the non-rephasing experiments (pulse order of $k_2$, $k_3$, $k_1$, and $k_{LO}$), $t_2$ was stepped from 0 to 1300 fs in 7 fs steps by moving $k_3$, $k_1$ (or alternately $k_2$), and for each $t_2$ delay, $t_3$ was stepped from 0 to 2200 fs in 14 fs steps by moving $k_{LO}$. The time domain data is Fourier transformed along the two stepped time delays to give the frequency domain spectra $S(\omega_i,\omega_j;t_k)$. The 2Q 2D IR spectra were linearly calibrated using azide ion in water, which has 0-1 and 0-2 frequencies at 2050 cm$^{-1}$ and 4075 cm$^{-1}$, respectively. Absolute value and real spectra are reported. The complex parts of the spectra are phased by a constant either using well-resolved transitions or setting the positive and negative peaks in each peak pair to equal but negative intensities.

The polarizations of all the excitation pulses are controlled with wire-grid polarizers placed before the sample. Polarizers after the sample select the polarization of the photon echo and local oscillator, and these are set to agreement with each other. Several sets of polarization conditions are used in this report and are listed in the order that the pulses follow in the experiment. Thus, polarizations <$p_1$, $p_2$, $p_3$, $p_{LO}$> were used for 1Q experiments and <$p_2$, $p_3$, $p_1$, $p_{LO}$> for 2Q experiments, where $p_n$ refers to the polarization of the pulse with wavevector $k_n$ and n being the laboratory defined laser pulse 1, 2, 3, or LO.

Figure 3:
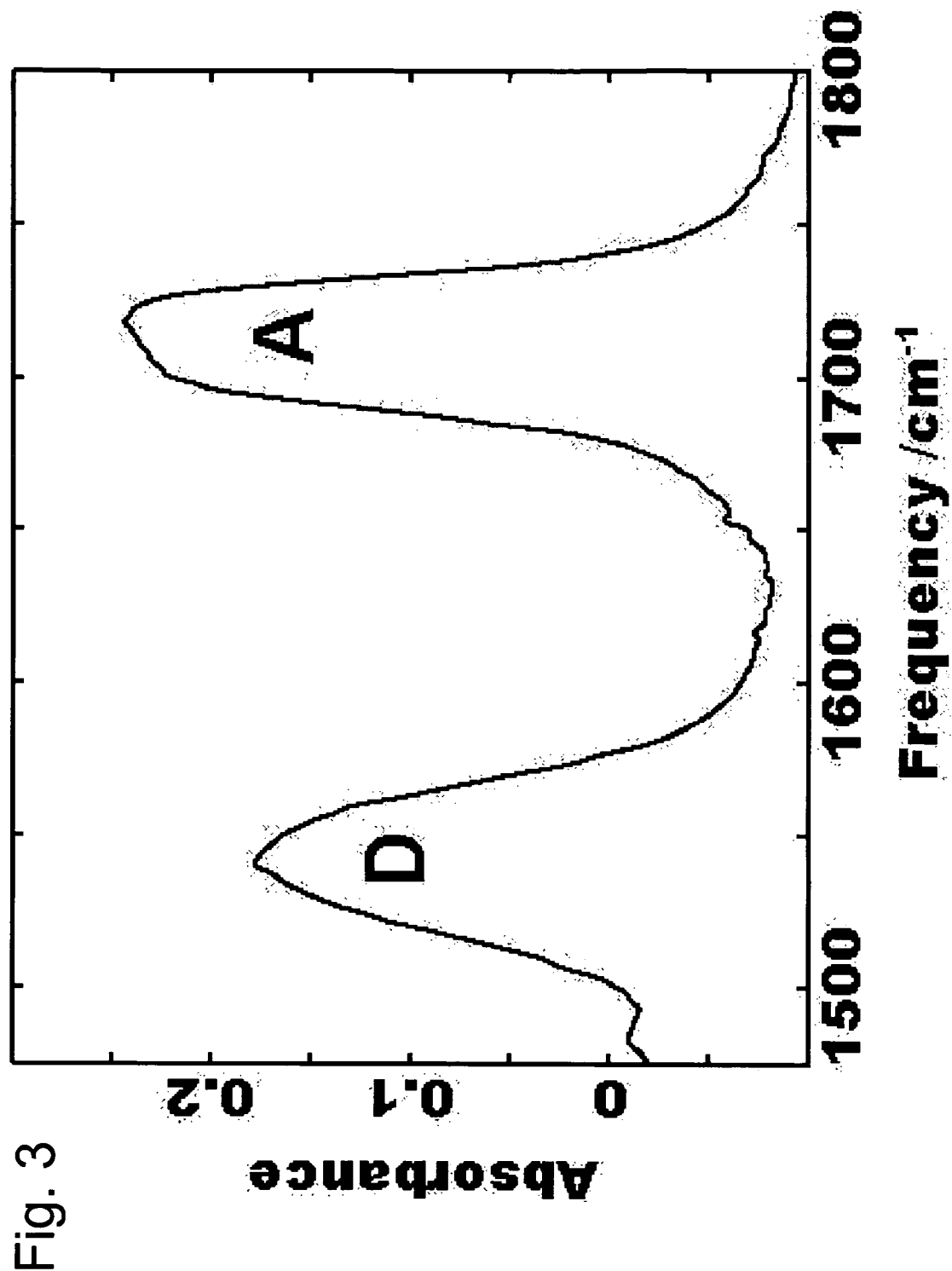
FIG. 3 provides a one dimensional spectrum of ethyl methylcarbamate in dimethylsulphoxide showing two principal peaks at 1710 cm$^{-1}$ and 1540 cm$^{-1}$, labeled A and D, respectively The peak at 1710 cm$^{-1}$ corresponds to the C=O stretch and the peak at 1540 cm$^{-1}$ corresponds to a primarily O—C—C vibrational mode.

FIG. 3 provides a one dimensional spectrum of ethyl methylcarbamate in dimethylsulphoxide showing two principal peaks at 1710 cm$^{-1}$ and 1540 cm$^{-1}$ labeled A and D, respectively. The peak at 1710 cm$^{-1}$ corresponds to the C=O stretch and the peak at 1540 cm$^{-1}$ corresponds to a primarily O—C—C vibrational mode.

Figure 4:
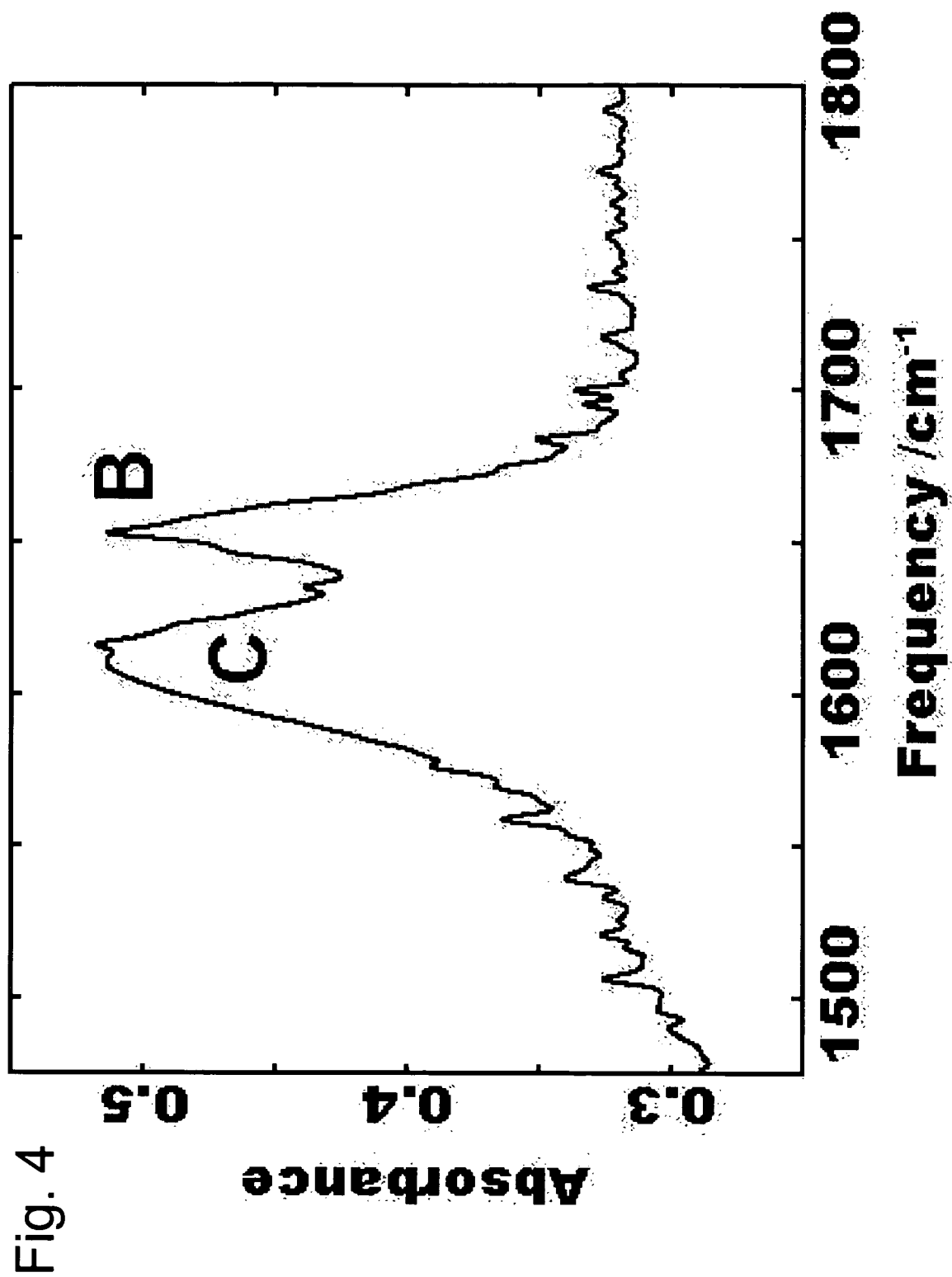
FIG. 4 provides a one dimensional spectrum of $^{13}$C urea in dimethylsulphoxide showing two principal peaks at 1660 cm$^{-1}$ and 1610 cm$^{-1}$. The peak at 1660 cm$^{-1}$ corresponds to the C=O carbonyl stretch vibrational mode and the peak at 1610 cm$^{-1}$ corresponds to C—N stretch vibrational mode.

FIG. 4 provides a one dimensional spectrum of $^{13}$C urea in dimethylsulphoxide showing two principal peaks at 1660 cm$^{-1}$ and 1610 cm$^{-1}$. The peak at 1660 cm$^{-1}$ corresponds to the C=O carbonyl stretch vibrational mode and the peak at 1610 cm$^{-1}$ corresponds to C—N stretch vibrational mode.

FIGS. 5A-E show absolute value 2D IR spectra of ethyl methylcarbamate and $^{13}$C-urea in dimethylsulphoxide collected with different pulse sequences, polarizations, and concentrations. A window function has been applied to the data. The contour lines shown in FIGS. 5A-5E correspond to intensity in arbitrary units and scaled to a value of 1. There are 120 contour lines from top to bottom for each figure. Peak positions are emphasized by the grey scale overlay provided in FIGS. 5A-5E.

Figure 5A:
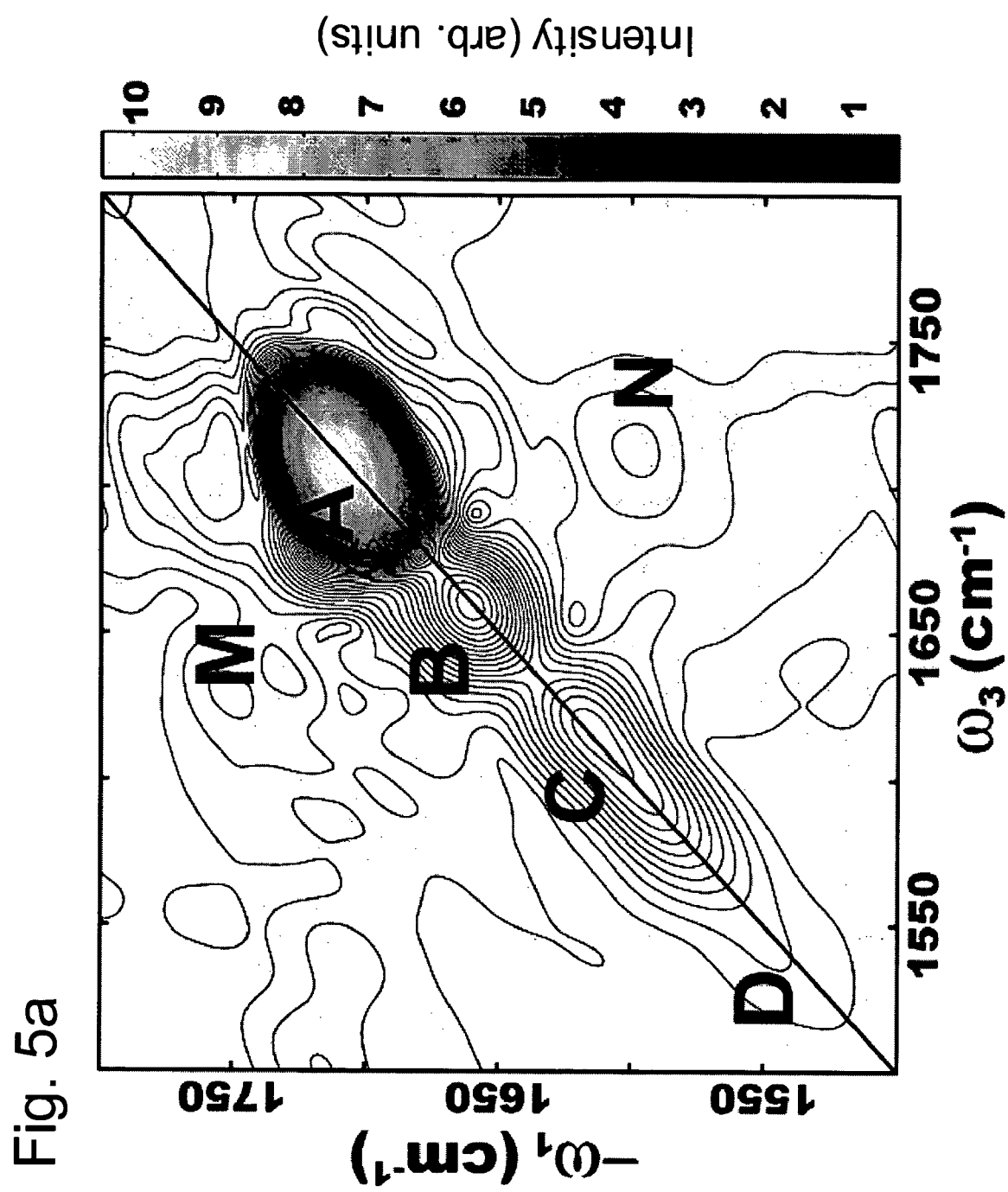
FIGS. 5A-E show absolute value 2D IR spectra of ethyl methylcarbamate and $^{13}$C-urea in dimethylsulphoxide collected with different pulse sequences, polarizations, and concentrations. A window function has been applied to the data. The contour lines shown in FIGS. 5A-5E correspond to intensity in arbitrary units and scaled to a value of 1. There are 120 contour lines from top to bottom for each figure. Peak positions are emphasized by the grey scale overlay provided in FIGS. 5A-5E.

FIG. 5A provides an absolute value 2D IR spectrum of 3 M ethyl methylcarbamate and 3M $^{13}$C-urea in dimethylsulphoxide taken with the four beams having the same polarization and using a one-quantum rephasing pulse sequence where the $k_1$ pulse comes before pulses $k_2$ and $k_3$. The peak labeled A at ($\omega_3$, $-\omega_1$)=(1710 cm$^{-1}$, 1710 cm$^{-1}$) is due to the 1710 cm$^{-1}$ ethyl methylcarbamate mode labeled A in FIG. 3. Peak B (1660, 1660) and peak C (1610, 1610) are the $^{13}$C-urea absorptions also seen in FIG. 4. Peak D at (1540, 1540) is the ethyl methylcarbamate mode labeled D in FIG. 3. The "diagonal" features A, B, C and D are the most intense features. The cross peaks are weaker. Representative cross peaks are labeled M and N that appear at approximately (1625, 1710) and (1710, 1610). Peak N is the strongest cross peak and peaks M and N are cross peaks between the $^{13}$C-urea and ethyl methylcarbamate.

Figure 5B:
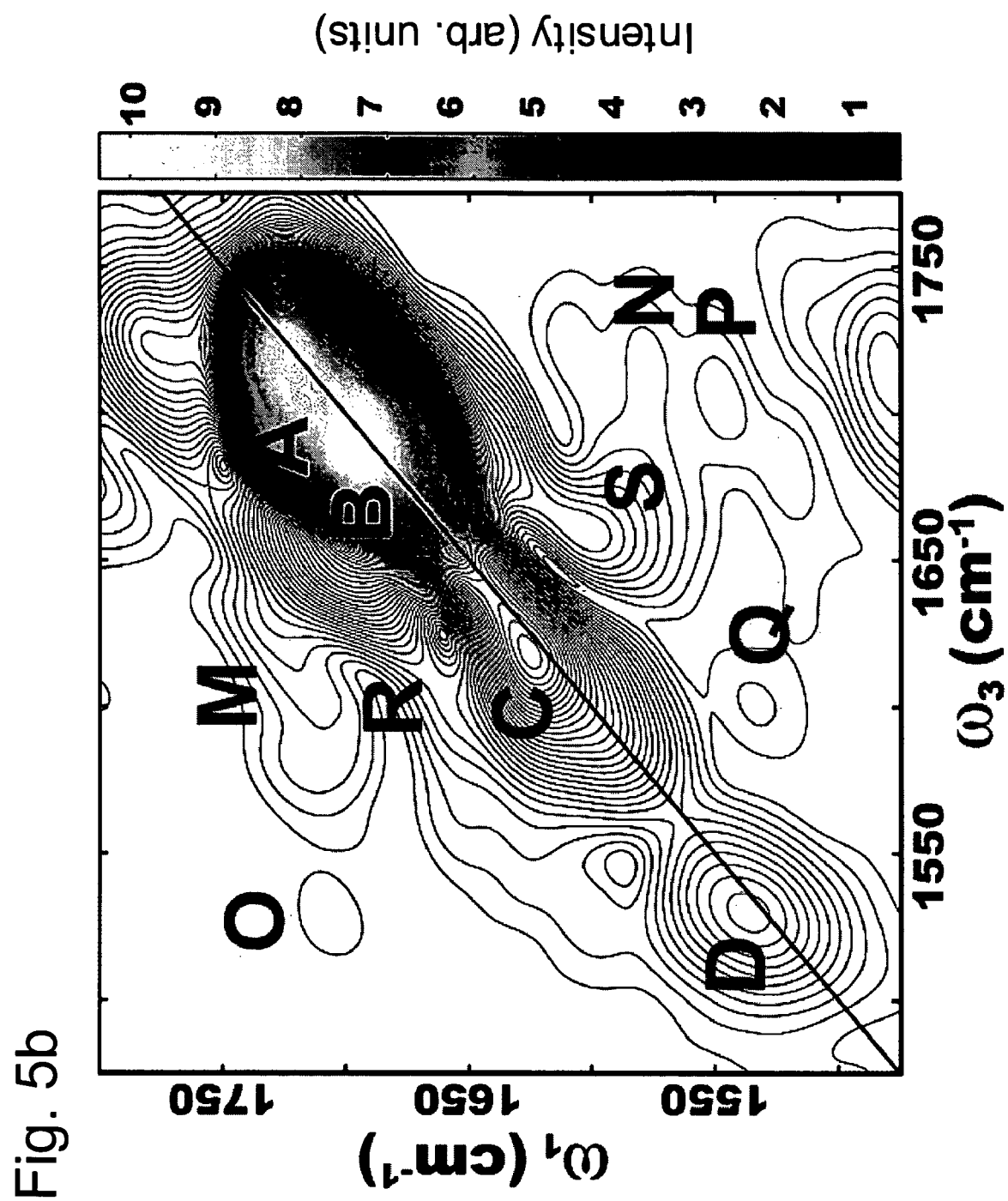

FIG. 5B provides an absolute value 2D IR spectrum of 3 M ethyl methylcarbamate and 3M $^{13}$C-urea in dimethylsulphoxide taken with the four beams having the same polarization and using a one-quantum non-rephasing pulse sequence where the $k_2$ pulse comes before pulses $k_1$ and $k_3$. The peak intensities and shapes are different than in FIG. 5A. Some cross peaks are better resolved, for example P. A new cross peaks appear that are labeled O, P, and Q at ($\omega_3$, $\omega_1$)=(1540, 1710), (1710, 1540), and (1600, 1540). Peaks O and P are due to coupling between peaks A and D of the ethyl methylcarbamate and peak Q is caused by coupling between the $^{13}$C-urea and ethyl methylcarbamate modes labeled C and D. A cross peak S (1660, 1610) is also now apparent, caused by intramolecular coupling between the urea absorptions B and C.

Figure 5C:
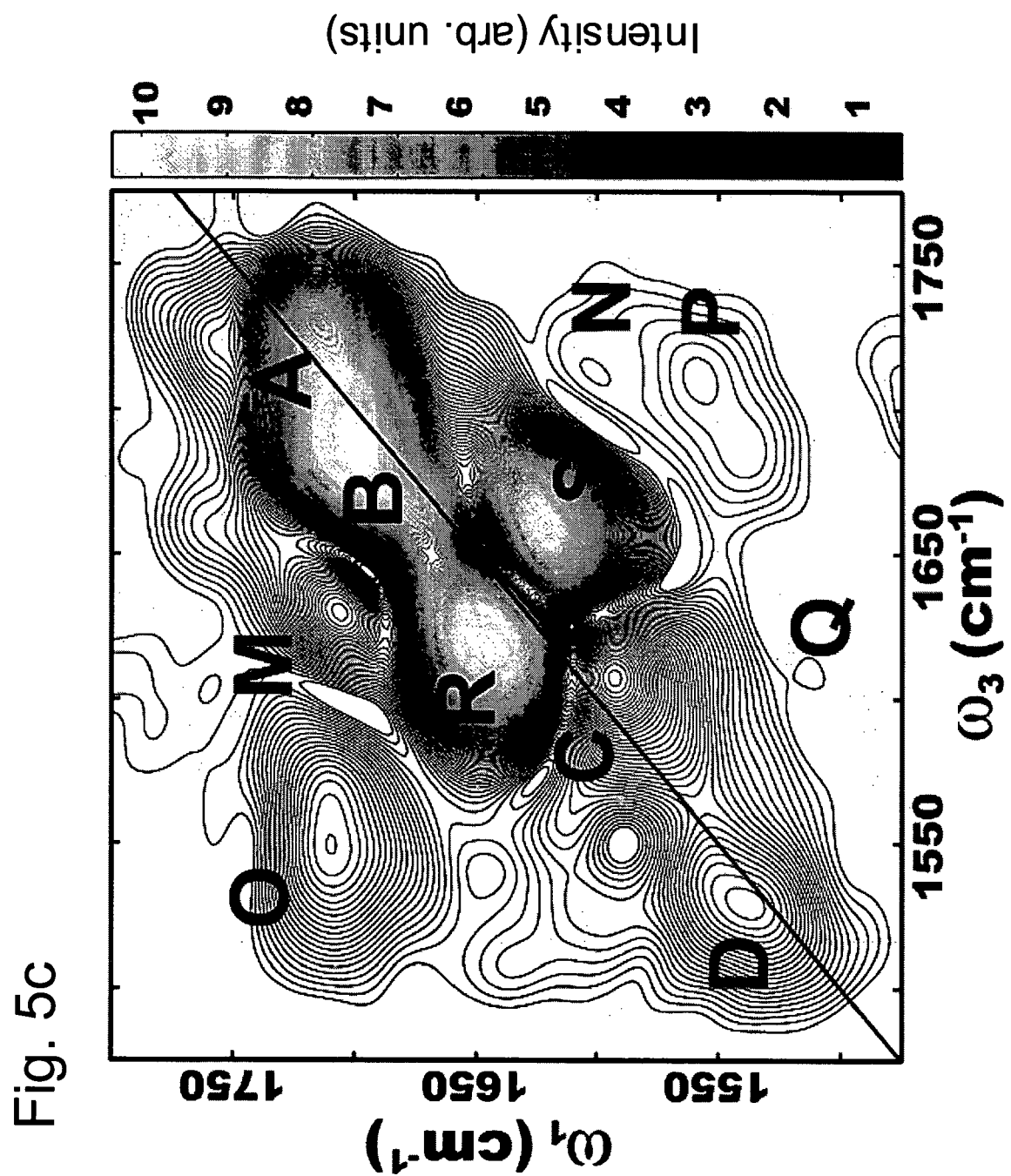

FIG. 5C provides an absolute value 2D IR spectrum of 3 M ethyl methylcarbamate and 3M $^{13}$C-urea in dimethylsulphoxide taken with the four beams having the polarizations 90°, −45°, +45° and 0° written in the order of $k_2$, $k_1$, $k_3$ and the local oscillator where the spectrum is collected using a one-quantum non-rephasing pulse sequence where the $k_2$ pulse comes before pulses $k_1$ and $k_3$. This polarization condition reduces the contributions from the diagonal peaks A, B, C and D and emphasizes the contributions from cross peaks that are generated from non-parallel transition dipoles. As a result, most cross peaks are much better resolved and much more intense relative to the maximum intensity of the spectrum. Peaks O and P are now more apparent, as are M and N. The most intense features are peaks R (1610, 1660) and S, caused by intramolecular coupling between the B and C $^{13}$C-urea absorptions.

Figure 5D:
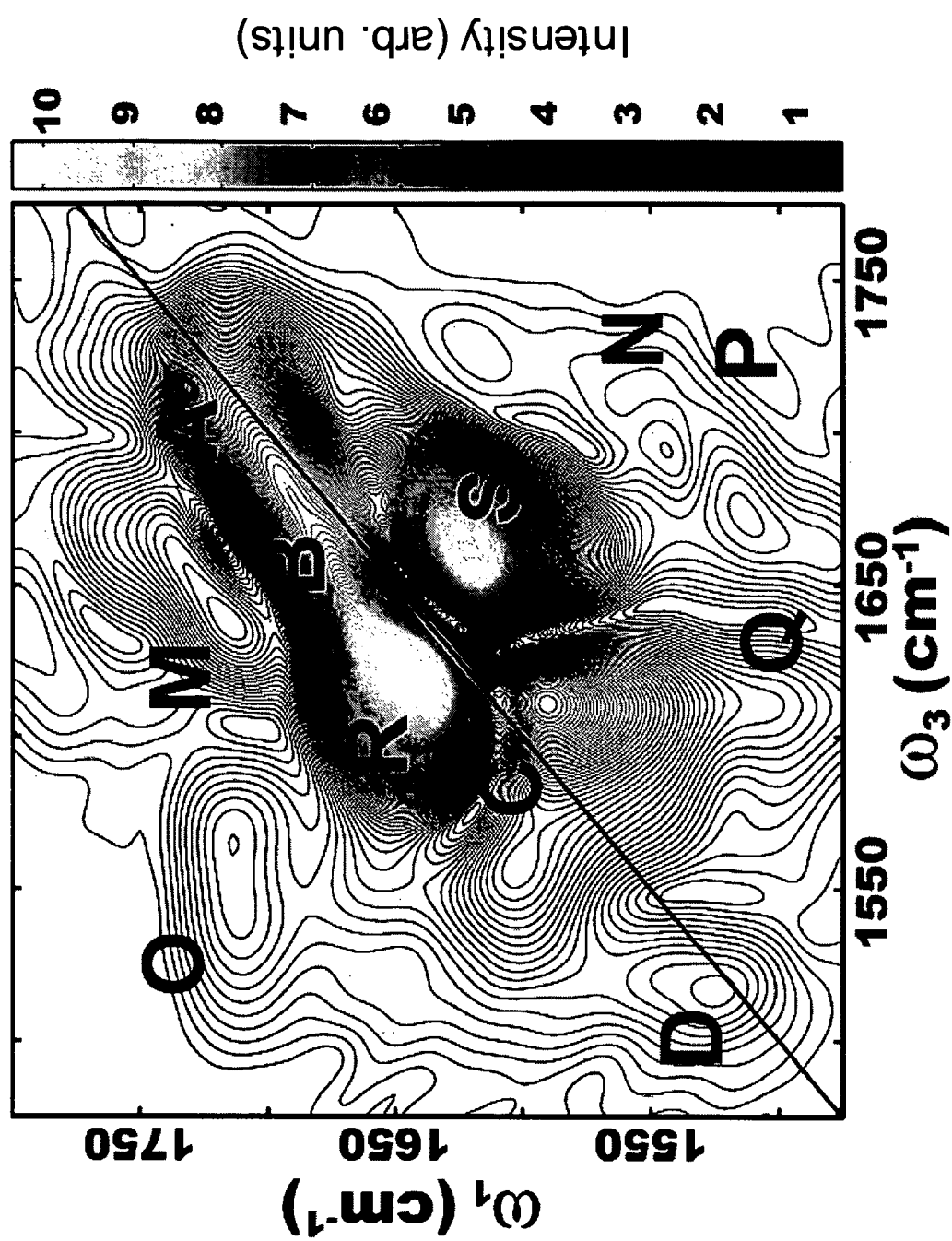

FIG. 5D provides an absolute value 2D IR spectrum of approximately 1M ethyl methylcarbamate and approximately 3M $^{13}$C-urea in dimethylsulphoxide taken with the four beams having the polarizations 90°, −45°, +45° and 0° written in the order of $k_2$, $k_1$, $k_3$ and the local oscillator where the spectrum is collected using a one-quantum non-rephasing pulse sequence where the $k_2$ pulse comes before pulses $k_1$ and $k_3$. The intensities of the ethyl methylcarbamate peaks decrease (A and D) as do cross peaks between the $^{13}$C-urea and ethyl methylcarbamate (M and N, for example).

Figure 5E:
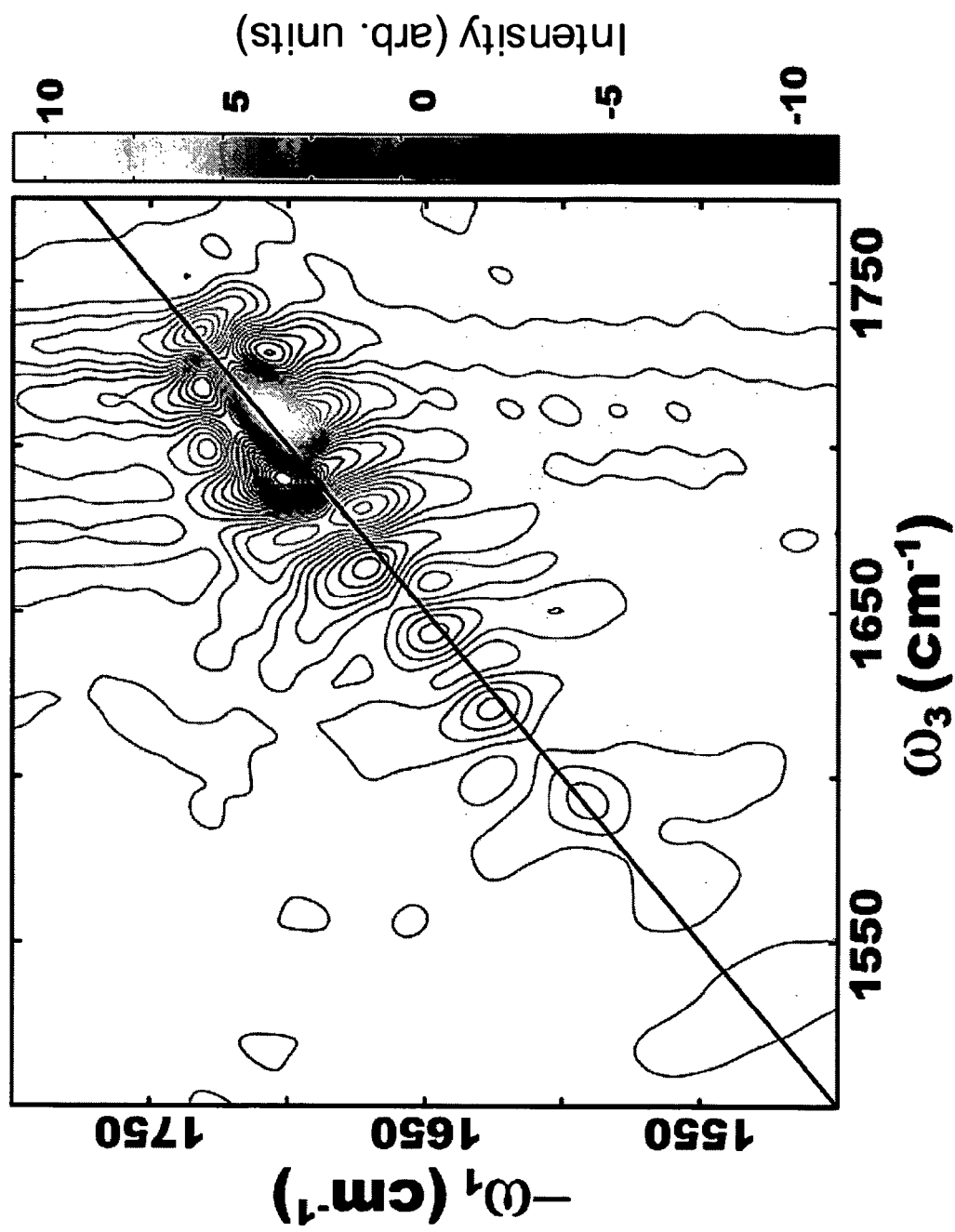

FIG. 5E provides an absolute value 2D IR spectrum generated by subtracting the complex parts of the data in FIGS. 5A and 5B. This procedure removes the phase twisting effects in the 2D IR spectra to generate absorptive features. Spectra with different beam polarizations and/or different pulse sequences can also be subtracted to enhance, suppress, or eliminate features, as is known to people familiar with the art.

Cross peaks M, N, O, P, and Q indicate that the vibrational modes of 13C-urea and ethyl methylcarbamate are coupled to or interacting with one another. This demonstrates that feasibility of this technique to monitor the interaction between two molecules that are weakly bound to one another. In addition to giving structural information on the bonding interaction between these two molecules, it also demonstrates the approach for high throughput screening. For example, if two of the pulses are narrowed to only be absorbed by the 1540 mode of ethyl methylcarbamate (peak D) and the third pulse is narrowed to only be absorbed by peak C of the 13C-urea, then the only signal measured would be that from peak Q. Thus, a setup in this manner would indicate that the 13C-urea and ethyl methylcarbamate are indeed interacting without the need to collect a full 2D IR spectrum. As a result, in principle, the signal would only have to be collected for a single repetition of the laser to ascertain that the 13C-urea and ethyl methylcarbamate are interacting. In practice, it may take a few laser shots to signal average and improve the signal-to-noise, or the signal might be collected for a background sample for comparison. Nonetheless, current laser repetition rates are 1-10 kHz, which means that the binding event can be ascertained in less than a few milliseconds under favorable conditions.

A complimentary measurement would be to monitor peaks O or P. Cross peaks O and P monitor the coupling between the two vibrational modes labeled A and D in ethyl methylcarbamate. Thus, they are sensitive to structural changes of ethyl methylcarbamate. Thus, if the structure or coupling or nature of the vibrations ethyl methylcarbamate changes with addition of 13C-urea, then the cross peak will change as well. This can be monitored with an entire 2D IR spectrum, or by narrowing two of the laser pulses on resonance with peak D and the third pulse on resonance with A, as above, in which case the change in signal can be ascertained with only one or a few laser repetitions.

The observation of cross peaks also indicates that it is possible to measure transient binding events that take place on a sub-millisecond and sub-microsecond timescale. The 13C-urea is well-known to be a very weak binder. As a result, the time that the 13C-urea is in contact or interacting with ethyl methylcarbamate is only the order of picoseconds to microseconds. It is difficult for other techniques, such as NMR to observe interactions that are sub-millisecond or sub-microsecond.

The observation that the cross peaks between the 13C-urea and ethyl methylcarbamate change with ethyl methylcarbamate concentration indicates that the 2D IR signal strength can be used to measure the binding affinity. To accomplish this, a series of spectra would be collected with varying concentrations of 13C-urea and ethyl methylcarbamate. Entire 2D IR spectra can be collected, as done here, or the laser pulses narrowed as has been described above to only collect signal from the desired cross peak.

A comparison of the spectra in FIGS. 5A-E shows that the intensity of cross peaks varies systematically with the concentration of the ethyl methylcarbamate. This result indicates that the methods of the present invention are useful for not only identifying the occurrence of an interaction, but also for characterizing an interaction in terms of thermokinetic parameters, such as the dissociation constant ($K_d$) or binding coefficient.

EXAMPLE 2

Multidimensional, Two-Color, Narrow-Band IR Spectroscopic Method for Characterizing Intramolecular Interactions The ability of the methods and devices of the present invention to detect and characterize interactions between modes of a given molecule using multiple pulses of various center frequencies was verified by experimental studies. Specifically, it is a goal of the present invention to provide multidimensional infrared spectroscopic techniques capable of detecting interactions by monitoring the changes associated with the vibrational modes of the candidate, target, or both. For example, by measuring the signal strength generated by three laser pulses, two of which are tuned to one vibrational mode and the third to a second vibrational mode in the same molecule in the presence and absence of the target and/or candidate binding interaction. The change of signal indicates binding, as discussed above.

Figure 6:
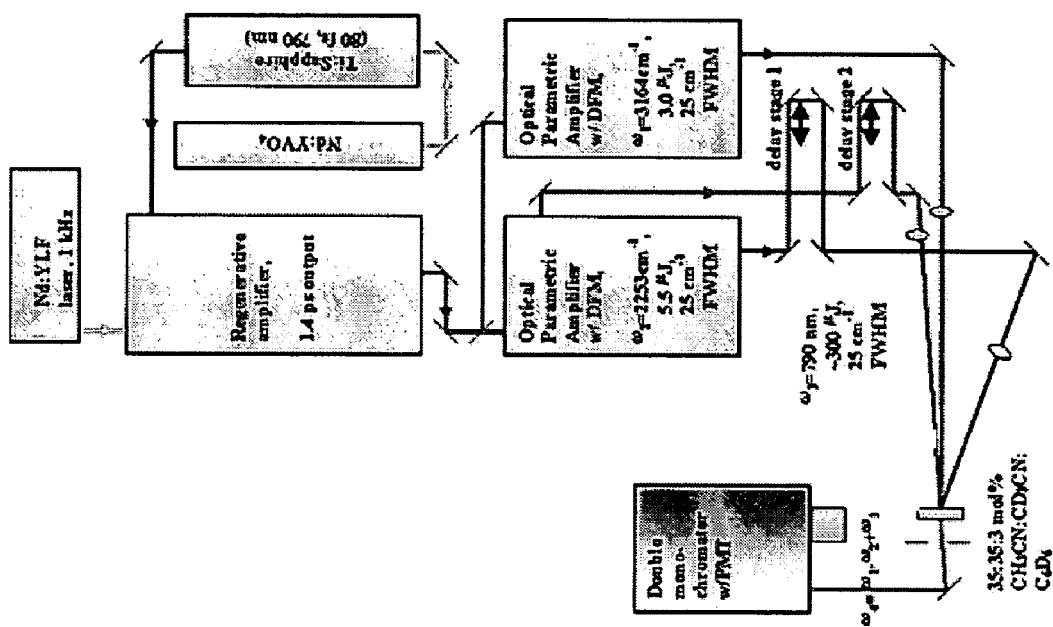
FIG. 6 shows a schematic diagram of the multidimensional spectroscopic apparatus used to carry out two-color, narrow-band IR spectroscopic experiments for characterizing intramolecular interactions in a solution containing $Ni(CO)_2(PPh_3)_2$.

The present invention includes method using mixed frequency and time domain techniques wherein the frequency resolution results from scanning the excitation lasers while monitoring the intensity of the output signal. Time delays between the excitation beams allow one to discriminate between different coherent processes and to coherently control the multidimensional spectrum. The experiments are performed using the system shown in FIG. 6. It is a Ti:sapphire-pumped dual-OPA system that creates two independently tunable 1 ps, 20 $cm^{-1}$ FWHM, vertically polarized infrared pulses with frequencies $\omega_1$ and $\omega_2$ using difference-frequency mixing of the signal and idler in a $AgGaS_2$ crystal. The two pulses are not phase coherent with each other. Their bandwidth is ~25 $cm^{-1}$ and their polarizations are parallel. The OPA $\omega_2$ output is split to create the $\vec{k}_2$ and $\vec{k'}_2$ beams and the three beams are focused with a parabolic mirror using either a $\vec{k}_s = \vec{k}_1 - \vec{k}_2 + \vec{k'}_2$ or $\vec{k}_s = -\vec{k}_1 + \vec{k}_2 + \vec{k'}_2$ phase matching geometry where $\vec{k}_s$ is the output signal. The output is isolated with an aperture and measured with a 0.3 m monochromator, a 2 $cm^{-1}$ bandwidth, and a single-element cooled MCT detector tuned to the output frequency. Two pyrometers monitored a weak reflection from a $CaF_2$ window in the path of each infrared beam in order to correct for intensity fluctuations. The output is re-collimated, sent through an aperture, and focused onto a cooled InSb detector. Two dimensional vibrational spectra are acquired by scanning $\omega_1$ for successive values of $\omega_2$.

Figure 7:
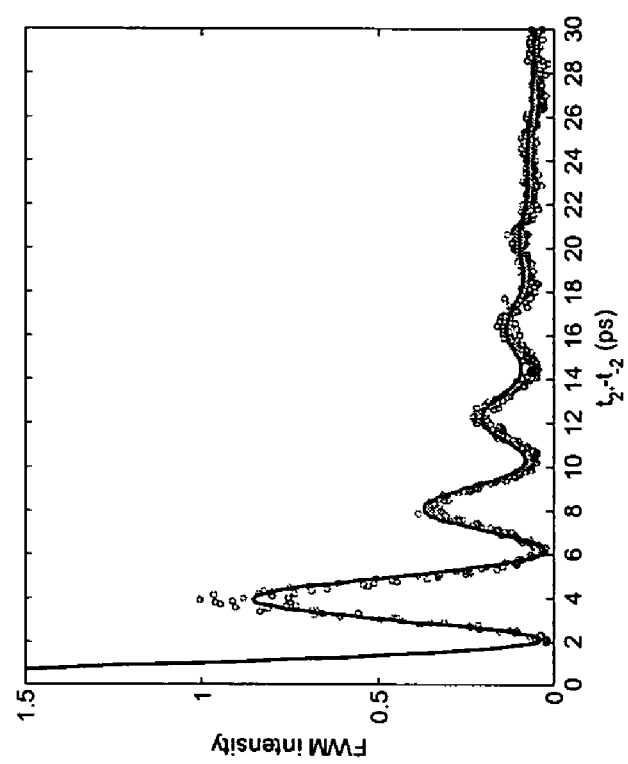
FIG. 7 shows two dimensional frequency domain vibrational spectra for both the $\vec{k}_s = \vec{k}_1 - \vec{k}_2 + \vec{k}_2'$ and $\vec{k}_s = -\vec{k}_1 + \vec{k}_2 + \vec{k}_2'$ phase-matching conditions.

The first results of this method used a sample of 0.010 M $Ni(CO)_2(PPh_3)_2$ in wet tetrahydrofuran. The strongest IR modes of $Ni(CO)_2(PPh_3)_2$ consist of a set of peaks at 1943 $cm^{-1}$ and 2002 $cm^{-1}$ (table 1). These modes are the antisymmetric and symmetric dicarbonyl stretching modes, respectively. In addition to this dicarbonyl complex, there is a tricarbonyl complex decomposition product that is also present and grows in time. This product produces new peaks appear at 1996 and 2068 $cm^{-1}$. The two dimensional frequency domain vibrational spectra are shown in FIG. 7 for both the $\vec{k}_s = \vec{k}_1 - \vec{k}_2 + \vec{k'}_2$ and $\vec{k}_s = -\vec{k}_1 + \vec{k}_2 + \vec{k'}_2$ phase-matching conditions. The spectrum with the $\vec{k}_s = \vec{k}_1 - \vec{k}_2 + \vec{k'}_2$ phase-matching consists of two sets of cross-peaks between the fundamentals at 1943 $cm^{-1}$ and 2002 $cm^{-1}$ and the peaks at 1996 $cm^{-1}$ and 2069 $cm^{-1}$. The diagonal peaks are single frequency triply vibrationally enhanced peaks and are expected to be very intense. The diagonal connecting the diagonal peaks in the $\vec{k}_s = \vec{k}_1 - \vec{k}_2 + \vec{k}'_2$ geometry spectrum has a slope nearly equal to 1. The 2D spectrum also contains two sets of cross-peaks—those involving the 1943 and 2002 cm$^{-1}$ modes of Ni(CO)$_2$(PPh$_3$)$_2$ and those involving the 1996 and 2068 cm$^{-1}$ modes of Ni(CO)$_3$PPh$_3$. The cross-peaks result from the triply vibrationally enhanced process and are a direct indication of intra-molecular vibrational coupling. Note that there are no observable cross-peaks between the Ni(CO)$_3$PPh$_3$ and the Ni(CO)$_2$(PPh$_3$)$_2$ modes. In the infrared spectrum, it is not possible to resolve the 1996 cm$^{-1}$ mode of Ni(CO)$_3$PPh$_3$ and the 2002 cm$^{-1}$ mode of Ni(CO)$_2$(PPh$_3$)$_2$. In the two dimensional spectrum, the cross-peaks clearly resolve the two contributions. One should also note that there is a weak solvent absorption band at 1967 cm$^{-1}$ that is present in the normal infrared spectrum but is absent in the FWM spectra. The discrimination against solvent features and the resolution of congested spectra are important characteristics of these coherent multidimensional vibrational spectroscopies.

The $\vec{k}_s = -\vec{k}_1 + \vec{k}_2 + \vec{k}'_2$ phase-matching spectrum was acquired with nearly the same sample and collection conditions. The diagonal peaks are as intense as in the $\vec{k}_s = \vec{k}_1 - \vec{k}_2 + \vec{k}'_2$ phase-matching spectrum. For the diagonal peaks, there is no difference in the two phase matching conditions because the two excitation frequencies are equal so one expects the same intensity. However, there is no evidence in the $\vec{k}_s = -\vec{k}_1 + \vec{k}_2 + \vec{k}'_2$ geometry for the cross-peaks that appear in the $\vec{k}_s = \vec{k}_1 - \vec{k}_2 + \vec{k}'_2$ geometry. The absence of the cross-peaks shows the importance of the phase-matching conditions and the resulting difference in mode coupling requirements in triply vibrationally enhanced experiments.

These experiments were performed with pulses that overlapped in time. The spectra are the result of contributions from many different time orderings of the pulses which coherently add to form the net output pulse. It is possible to use the time delays between optical pulses and a frequency selective monochromator to spectrally resolve the output frequency so one can pick a particular coherence pathway. The demonstration of this capability used carbon disulfide samples as a model to demonstrate the feasibility. The sample consists of a 100-micron thick 0.3 mol % CS$_2$: 99.7% CH$_2$Cl$_2$ solution sandwiched between two 3-mm optically smooth CaF$_2$ windows. The $\omega_1$ value is tuned near the $v_1 + v_3$ combination band at 2170 cm$^{-1}$ and the $\omega_2$ value is tuned near the $v_3$ fundamental at 1520 cm$^{-1}$. Note also that ($\omega_1 - \omega_2$) is near the $v_1$ fundamental at 660 cm$^{-1}$.

In these mixed frequency/time domain methods, it is important to realize that the pulses' temporal widths are similar to the coherence dephasing times so the response function lies between the cw and impulsive limits. The output frequency can differ in each limit. The cw limit corresponds to a "forced oscillator" model where the output coherence frequency is defined by the linear combination of the excitation field frequencies. Since the excitation line width is narrow and lies within the bandwidth of the molecular transition, the multidimensional spectrum is recorded in the frequency domain. The impulsive limit corresponds to the "free induction decay" model where the output coherence radiates at its natural frequency. Since most of the excitation energy lies outside the bandwidth of the molecular transition, the multidimensional spectrum is recorded in the time domain. Simulations of our experiments show that the output signal has important contributions from both the "forced oscillator" and the "free induction decay".

Since our experiments have only two tunable frequencies (labeled $\omega_1$ and $\omega_2$), 9 of the possible 12 coherence pathways are triply resonant while the other 4 are singly resonant. Under the conditions of our experiment, one would predict triply vibrationally enhanced peaks at four positions—($\omega_1$, $\omega_2$, $\omega_m$)=(2170, 1520, 2170), (2170, 1500, 2170), (2150, 1520, 2150), and (2170, 1510, 2170) cm$^{-1}$. These positions correspond to the ground state transitions to $v_3$ and $v_1 + v_3$ at 1520 and 2170 cm$^{-1}$, respectively, and the excited state transitions $v_1 + v_3 \rightarrow v_1 + 2v_3$ and $v_3 \rightarrow v_1 + 2v_3$ that are anharmonically shifted by w to 1500 and 2150 cm$^{-1}$, respectively. In addition, there is a fully resonant peak at the 1510 cm$^{-1}$ position from a $v_1 + v_3 \rightarrow v_3$ transition that is anharmonically shifted from the ground state transition. There are two or three possible peak positions for the pathways that are not fully resonant. These peak positions depend upon the excitation frequency bandwidths of $\omega_1$ and $\omega_2$ and the size of the "forced oscillator" or "free induction decay" contributions.

Figure 8:
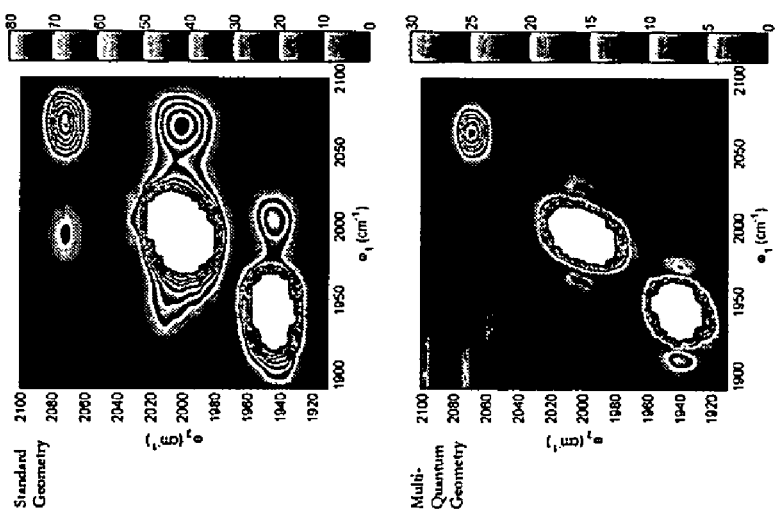
FIG. 8 shows the spectra where the monochromator frequency and excitation pulse delays together select for specific pathways.

FIG. 8 shows the spectra where the monochromator frequency and excitation pulse delays together select for specific pathways. As shown in FIG. 8, the position of the peak changes depending upon which pathway is enhanced by the selection of delays and monochromator position. All of the triply resonant pathways have peaks at or close to the positions expected from the resonances. The doubly resonant peaks are not at defined positions because there are two or three sets of resonant states that can provide double resonances that interfere and shift the expected peak positions. Simulations show how the different double resonances and the interfering pathways are predicted to interfere and generate the observed peak.

Figure 9:
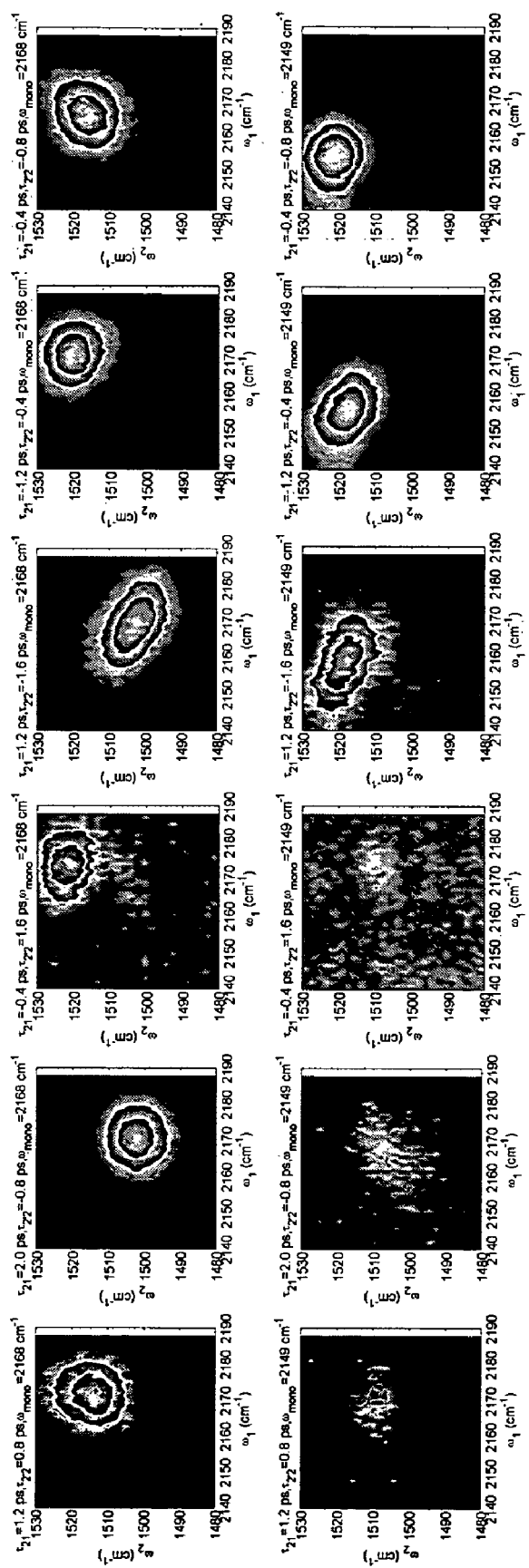
FIG. 9 shows a plurality of two dimensional frequency domain vibrational spectra which demonstrate how the intensity is modulated by the choice of the time delay.

One can also achieve coherent control of the relative intensities of spectral features in multidimensional spectra. Here, the choice of the time delays can create situations where two or more pathways coherently interfere to either enhance a particular spectral feature or discriminate against it. FIG. 9 shows a plurality of two dimensional frequency domain vibrational spectra which demonstrate how the intensity is modulated by the choice of the time delay. In the invention, suitable experimental conditions can be established that enhance peaks that are signatures of protein binding and discriminate against peaks that can interfere with the measurement.

EXAMPLE 3

Multidimensional IR-Visible Spectroscopic Methods for Identifying and Characterizing Molecular Interactions In the present invention coherent multidimensional vibrational spectra may be generating using two infrared transitions that provide a doubly vibrationally enhancement of the output signal and a Raman transition that can also be electronically resonant. We have used the mixed frequency domain and time domain ultrafast system as described in Example 2 and we have also used a simpler nanosecond frequency domain system. In this system, an injection seeded Nd:YAG laser excites a dual optical parametric oscillator/amplifier (OPO/OPA) which produces two infrared outputs at frequencies of $\omega_1$ and $\omega_2$ that are independently tunable from ca. 2150-4550 cm$^{-1}$. The infrared beams and the residual 532 nm light (labeled $\omega_3$) from the frequency doubled Nd:YAG laser are separately focused into the sample. The angles between the beams are adjusted for phase matching. The new beams that are created in the sample are isolated with apertures and directed into a double monochromator. The frequencies of the OPO/OPA's and the monochromator are controlled with a computer so the relationship $\omega_4=\omega_1-\omega_2+\omega_3$ is always maintained. The signal intensities are measured with a photomultiplier and stored in a computer.

In order to generate 2D DOVE spectra, the infrared frequencies were tuned to the region of appropriate vibrational features. One frequency was fixed while the second frequency was scanned across the spectral region. The first frequency was then incremented to a new value and another spectrum was obtained. This process was repeated until a full set of spectra were obtained over the entire region of interest. In order to lessen complications from the changing absorption and refractive indices in a spectral scan, the frequency for scanning was chosen to correspond with the spectral region with the weakest absorption features.

Figure 10:
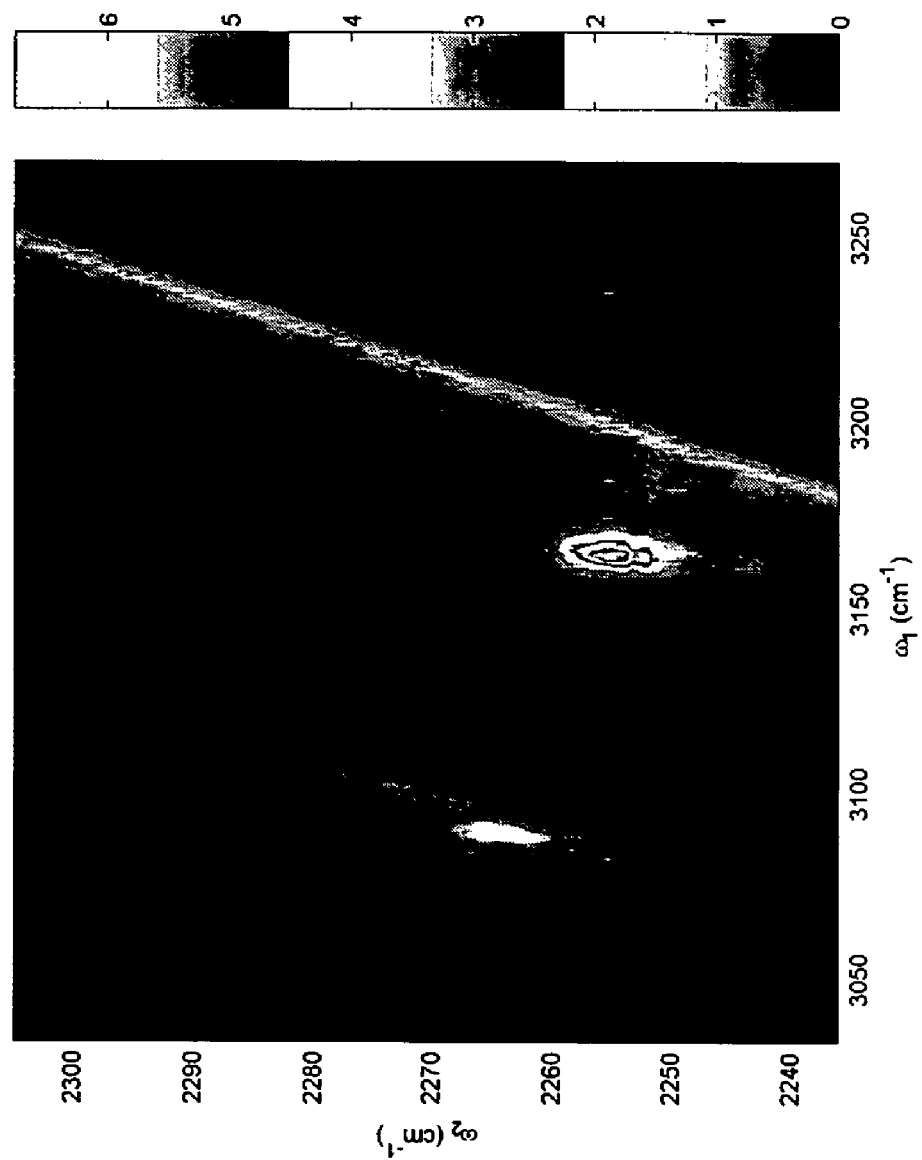
As shown in FIG. 10, the position of the peak changes depending upon which pathway is enhanced by the selection of delays and monochromator position.

An example of this method's performance uses a mixture of acetonitrile ($CH_3CN$), deuterated acetonitrile ($CH_3CN$), and deuterated benzene ($C_6D_6$). The two dimensional spectrum of this mixture is shown in FIG. 10. The x and y axes are the $\omega_1$ and $\omega_2$ frequencies and the z axis is the $\omega_4$ output intensity. The diagonal features are coherent Raman resonances that correspond to the $v_4$ vibrations of $CD_3CN$ and $CH_3CN$ at the difference frequencies $\omega_1-\omega_2=832$ and 917 $cm^{-1}$, respectively. The $v_2$ vibration of $C_6D_6$ at $\omega_1-\omega_2=944$ $cm^{-1}$ was used to scale the spectrum. The strongest double resonances occurred when co, was resonant with the combination band $v_2+v_4$ and $\omega_2$ was simultaneously resonant with the $v_2$ vibration. For $CH_3CN$ this occurred at $\omega_1=3166/\omega_2=2255$ $cm^{-1}$ and for $CD_3CN$ at $\omega_1=3094/\omega_2=2264$ $cm^{-1}$. The absence of cross peaks at $\omega_1=3166/\omega_2=2264$ $cm^{-1}$ and $\omega_1=3094/\omega_2=2255$ $cm^{-1}$ demonstrates the excellent molecular selectivity that can be achieved by this technique. There is a weaker double resonance occurs when co, is resonant with the combination band $v_3+2v_4$ and $\omega_2$ is simultaneously resonant with the $v_3+v_4$ combination band. For $CH_3CN$ this occurs at $\omega_1=3203/\omega_2=2294$ $cm^{-1}$. A very weak feature appears when $\omega_1$ is resonant with the combination band $v_2+v_4$ and $\omega_2$ is simultaneously resonant with the $v_3+v_4$ combination band. For $CH_3CN$ this occurs at $\omega_1=3166/\omega_2=2944$ $cm^{-1}$. There is a strong DOVE-IR peak at $\omega_1=3200$ and $\omega_2=2293$ $cm^{-1}$ corresponding to a double resonance involving the $v_2+v_4$ combination band and the $v_2$ mode, respectively. There is a weak DOVE-IR peak at $\omega_1=3200$ and $\omega_2=2293$ $cm^{-1}$ corresponding to a double resonance involving the $v_3+2v_4$ and the $v_3+v_4$ combination bands, respectively. There is also a strong diagonal ridge that falls at a constant value of $\omega_1-\omega_2=944$ $cm^{-1}$ corresponding to the normal $C_6D_6$ Raman transition. All the spectra in FIG. 10 were normalized to that Raman line.

There are also features in the spectrum from doubly vibrationally enhanced Raman processes. These Raman processes have slightly different energies due to anharmonicities that shift the frequencies of the combination bands. For $CH_3CN$, in addition to the cross-peak when $v_1$ is resonant with the $v_2+v_4$ combination band and $\omega_2$ is resonant with the $v_2$ vibration at 2255 $cm^{-1}$, there is also a cross-peak from the doubly vibrationally enhanced Raman process when the difference frequency $\omega_1-\omega_2$ is resonant with the $v_4$ vibration. This resonance occurs when $\omega_2=2249$ $cm^{-1}$. For $CD_3CN$ the equivalent occurs at $\omega_1=3094/\omega_2=2262$ $cm^{-1}$. In addition, there is a second weaker ridge that falls at a constant value of $\omega_1-\omega_2=918$ $cm^{-1}$ and corresponds to the $CH_3CN$ $v_4$ C—C stretch mode. It undergoes enhancements when $\omega_1$ reaches 3164 and 3200 $cm^{-1}$. The first enhancement corresponds to a from doubly vibrationally enhanced Raman process involving the $v_2+v_4$ combination band and the $v_4$ Raman band. The second enhancement corresponds to a from doubly vibrationally enhanced Raman process involving the $v_3+2v_4$ combination band and the $v_4$ Raman band.

One of the most important characteristics of these methods is their ability to discriminate against modes that are not coupled. The importance arises because the only cross-peaks that can occur in a spectrum are those associated with modes that are coupled by intra- or intermolecular interactions, so these methods selectively target interactions. There may be strong fundamental peaks or solvent contributions that usually obscure the weaker features in normal 1-D spectra but these should not interfere if they are not coupled to the features of interest.

The capabilities of these methods for spectrally selecting and resolving the spectra of individual components in a multi-component sample are demonstrated in FIG. 10, which shows two well-resolved DOVE peaks corresponding to double resonances with $CH_3CN$ and $CD_3CN$ and there are no cross-peaks between them. This demonstration shows that DOVE methods have the capability to dissect a 1-D spectrum into the individual spectra of each component, isotopic composition, or molecular conformer.

Infrared spectroscopy of biological systems is often limited by strong water absorption which obscures the vibrational spectra of proteins and other materials that may be present in the solvent. In order to establish the applicability of 2D DOVE methods to biological systems, we examined $CH_3CN/H_2O$ mixtures. The water bands near 3164 $cm^{-1}$ are very strong and obscure the much weaker $CH_3CN$ combination bands. However, the 2D spectra show only the cross-peak from the $CH_3CN$. The water does not contribute appreciably for several reasons. There are no interacting infrared modes of water at the two frequencies being used and the Raman transition that would be required from the water is weak. In fact, water is one of the weakest Raman scatters, presumably because its electronic states are very energetic. This demonstration shows that the present techniques and measurements are applicable to experimental conditions comparable to most biological systems, such as in vivo conditions.

EXAMPLE 4

Methods of Modeling 2D-IR Spectra

In addition to use in high-throughput screening applications, the device can be used to gain structural and dynamical information on the molecules and binding interactions of interest and which would serve to aid in rational drug design, for instance. Methods for measuring and interpreting non-linear spectra are well-documented in the literature and are self-apparent to experts in the field. Particularly, methods of measuring and interpreting multidimensional IR spectra are described in C. Fulmer, P. Mukherjee, T. Krummel and M. Zanni, "A pulse sequence for directly measuring the anharmonicities of coupled vibrations: Two-quantum two-dimensional infrared spectroscopy," *The Journal of Chemical Physics*, May 1, 2004, Volume 120, Issue 17, pp. 8067-8078, Abramavicius, D. and S. Mukamel (2004). "Disentangling multidimensional femtosecond spectra of excitons by pulse shaping with coherent control." *J. Chem. Phys.* 120(18): 8373-8378; Chernyak, V., W. M. Zhang, et al. (1998). "Multidimensional femtosecond spectroscopies of molecular aggregates and semiconductor nanostructures: the nonlinear exciton equations." *J. Chem. Phys.* 109(21): 9587-9601; Cho, M. (2001). "Nonlinear response functions for the three-dimensional spectroscopies." *J. Chem. Phys.* 115(10): 4424-4437; Cho, M. (2002). "Ultrafast vibrational spectroscopy in condensed phases." *Phys. Chem. Comm.* 5(7): 40-58; Choi, J.-H., S. Ham, et al. (2002). "Inter-peptide interaction and delocalization of amide I vibrational excitons in myoglobin and flavodoxin." *J. Chem. Phys.* 117: 6821-6832; Demirdoven, N., M. Khalil, et al. (2002). "Correlated vibrational dynamics revealed by two-dimensional infrared spectroscopy." *Phy. Rev. Lett.* 89(23): 237401/1-237401/4; Fulmer, E. C., P. Mukherjee, et al. (2004). "A pulse sequence for directly measuring the anharmonicities of coupled vibrations: two-quantum two-dimensional infrared spectroscopy." *J. Chem. Phys.* 120(17): 8067-8078; Gnanakaran, S. and R. M. Hochstrasser (2001). "Conformational preferences and vibrational frequency distributions of short peptides in relation to multidimensional infrared spectroscopy." *J. Amer. Chem. Soc.* 123: 12886-12898; Gnanakaran, S., R. M. Hochstrasser, et al. (2004). "Nature of structural inhomogeneities on folding a helix and their influence on spectral measurements." *Proc. Nat. Acad. Sci. USA* 101(25): 9229-9234; Ham, S. and M. Cho (2003). "Amide I modes in the N-methylacetamide dimer and glycine dipeptide analog: diagonal force constants." *J. Chem. Phys.* 118(15): 6915-6922; Ham, S., S. Hahn, et al. (2004). "Amide I modes of alpha-helical polypeptide in liquid water: conformational fluctuation, phase correlation, and linear and nonlinear vibrational spectra." *J. Phys. Chem. B* 108: 9333-9345; Hamm, P., M. Lim, et al. (1998). "Structure of the Amide I band of peptides measured by femtosecond nonlinear-infrared spectroscopy." *J. Phys. Chem. B* 102: 6123-6138; Khalil, M., N. Demirdoven, et al. (2004). "Vibrational coherence transfer characterized with Fourier-transform 2D IR spectroscopy." *J. Chem. Phys.* 121 (1): 362-373; Krummel, A. T., P. Mukherjee, et al. (2003). "Inter- and intra-strand vibrational coupling in DNA studied with heterodyned 2D IR spectroscopy." *J. Phys. Chem. B* 107: 9165; Moran, A. and S. Mukamel (2004). "The origin of vibrational mode couplings in various secondary structural motifs of polypeptides." *Proc. Natl. Acad. Sci. U.S.A.* 101: 506-510; Mukherjee, P., A. T. Krummel, et al. (2004). "Site-specific vibrational dynamics of the CD3zeta membrane peptide using heterodyned two-dimensional infrared photon echo spectroscopy." *J. Chem. Phys.* 120(21): 10215-10224; Paul, C., J. Wang, et al. (2004). "Vibrational coupling, isotopic editing, and beta-sheet structure in a membrane-bound polypeptide." *J. Amer. Chem. Soc.* 126: 5843-5850; Scheurer, C. and S. Mukamel (2001). "Design strategies for pulse sequences in multidimensional optical spectroscopies." *J. Chem. Phys.* 115(11): 4989-5004; Scheurer, C. and S. Mukamel (2002). "Infrared analogs of heteronuclear nuclear magnetic resonance coherence transfer experiments in peptides." *J. Chem. Phys.* 116(15): 6803-6816; Scheurer, C., A. Piryatinski, et al. (2001). "Signatures of b-peptide unfolding in two-dimensional vibrational echo spectroscopy: a simulation study." *J. Amer. Chem. Soc.* 123(13): 3114-3124; Venkatramani, R. and S. Mukamel (2002). "Correlated line broadening in multidimensional vibrational spectroscopy." *J. Chem. Phys.* 117(24): 11089-11101; Wang, J. and R. M. Hochstrasser (2003). "Characteristics of the two-dimensional infrared spectroscopy of helices from approximate simulations and analytic models." *Chem. Phys.* 297: 195-219. All of these references and all references cited in these references are hereby incorporated by reference in their entireties to the extent not inconsistent with the present description.

The theoretical descriptions and simulations described in the manuscripts referenced above are general in that they can be applied to all types of molecules including biomolecules, inorganic compounds, and organic compounds. They can also be expanded to include higher order spectroscopies, pulse shaping techniques, different pulse delays, polarizations, pulse intensities, cascading effects, multiple laser beams, multiple center frequencies and bandwidths, or any combination of these and other effects.

We claim:

1. A method for identifying the occurrence of an interaction involving a first molecule and a second molecule, the method comprising the steps of:
    a) providing the first molecule;
    b) contacting the first molecule with the second molecule;
    c) directing onto the first molecule and the second molecule a first coherent light having a first selected wavelength and a second coherent light having a second selected wavelength that is different from the first selected wavelength, wherein the first and second coherent lights have spatially separated propagation axes that intersect at the first molecule, and wherein the first and second coherent lights excite molecular vibrations in the first molecule or the second molecule or both the first and the second molecules;
    d) detecting a signal beam of light propagating along an axis that is spatially separated from the propagation axes of the first and second coherent lights, the signal beam of light resulting from the interaction of the first and second molecules in the presence of the first and second coherent lights, wherein the signal beam of light has an intensity, an amplitude, and a polarization; and
    e) identifying the occurrence of the interaction involving the first molecule and the second molecule based on the presence of the signal beam.

2. The method of claim 1 wherein the first and second coherent lights have temporal profiles.

3. The method of claim 2 wherein each of the temporal profiles of the first and second coherent lights has two intensity maxima or three intensity maxima.

4. The method of claim 1 wherein the first coherent light has a first wavelength distribution and the second coherent light has a second wavelength distribution, and wherein the first wavelength distribution is different from the second wavelength distribution.

5. The method of claim 1 wherein the first coherent light is directed onto the first and second molecules at a first time, the second coherent light is directed onto the first and second molecules at a second time, wherein the second time is after the first time, and wherein the second time is a selected first delay after the first time.

6. The method of claim 5 further comprising the step of directing a third coherent light having a third selected wavelength onto the first and second molecules.

7. The method of claim 6, wherein the third coherent light is directed onto the first and second molecules at a third time, wherein the third time is after the second time, and wherein the third time is a selected second delay after the first time.

8. The method of claim 7, further comprising recording the intensity, amplitude, or polarization of the signal beam of light as a function of both the selected first delay time and the selected second delay time to produce a two dimensional spectrum.

9. The method of claim 1 wherein the first selected wavelength is resonant with a first vibrational mode of the first molecule and wherein the second selected wavelength is resonant with a second vibrational mode of the first molecule, or wherein the first selected wavelength is resonant with a first vibrational mode of the second molecule and wherein the second selected wavelength is resonant with a second vibrational mode of the second molecule.

10. The method of claim 1 wherein the first selected wavelength is resonant with a vibrational mode of the first molecule and wherein the second selected wavelength is resonant with a vibrational mode of the second molecule.

11. The method of claim 1, further comprising the step of contacting the first molecule with a competitive binding reference molecule before contacting the first molecule with the second molecule, after the first molecule is contacted with the competitive binding reference molecule, further comprising the steps of
   directing onto the first molecule and the competitive binding reference molecule the first coherent light having a first selected wavelength and the second coherent light having a second coherent wavelength, wherein the first and second coherent lights excite molecular vibrations in either the first molecule, the competitive binding reference molecule or both the first and the competitive binding reference molecules;
   detecting a competitive binding signal beam of light propagating along an axis that is spatially separated from the propagation axes of the first and second coherent lights, the competitive binding signal beam of light resulting from the interaction of the first molecule and the competitive binding reference molecule in the presence of the first and second coherent lights, wherein the competitive binding signal beam of light has an intensity, an amplitude, and a polarization; and
   identifying the occurrence of the interaction involving the first molecule and the competitive binding reference molecule based on the presence of the competitive binding signal beam of light.

12. The method of claim 11 wherein the first selected wavelength is resonant with a vibrational mode of the first molecule and wherein the second selected wavelength is resonant with a vibrational mode of the competitive binding reference molecule.

13. The method of claim 11 further comprising the steps of:
   measuring the intensity of the competitive binding signal beam of light and establishing a value of the intensity of the competitive binding signal beam of light ($I_1$);
   measuring the intensity of the signal beam of light and establishing a value of the intensity of the signal beam of light ($I_2$); and
   comparing the value of the intensity of the competitive binding signal beam of light to the value of the intensity of the signal beam of light, wherein the presence of a measurable difference between $I_1$ and $I_2$ provides quantitative information relating to the nature of the interaction between the first molecule and the second molecule in the presence of the competitive binding reference molecule.

14. The method of claim 11 wherein the amplitude of the competitive binding signal beam is an amplitude of the electric field of the competitive binding signal beam and further comprising the steps of:
   measuring the amplitude of the electric field of the competitive binding signal beam of light and establishing a value of the amplitude of the electric field of the competitive binding signal beam of light ($E_1$);
   measuring the amplitude of the electric field of the signal beam of light and establishing a value of the amplitude of the electric field of the signal beam of light ($E_2$); and
   comparing the value of the amplitude of the electric field of the competitive binding signal beam of light to the value of the amplitude of the electric field of the signal beam of light, wherein the presence of a measurable difference between $E_1$ and $E_2$ provides quantitative information relating to the nature of the interaction between the first molecule and the second molecule in the presence of the competitive binding reference molecule;
   comparing the value of the amplitude of the electric field of the competitive binding signal beam to the value of the amplitude of the electric field of the signal beam, wherein a measurable difference ($E_1-E_2$) indicates the occurrence of an interaction involving a first molecule and a second molecule.

15. The method of claim 1 wherein the first molecule or the second molecule is labeled with a vibrational tag.

16. The method of claim 15 wherein the vibrational tag is a molecular species selected from the groups consisting of: an azido group; a cyano group; an aliphatic diazo group; a cynate group; a thiocynate group; a ketene group; an isocyanate group; an isothiocyanate group; an aminonitrile group; an isonitrile group; a carbonyl group; a mono-substituted acetylene group; a di-substituted acetylene group; a nitrile group; an acrylonitrile group; a group having a carbon deuterium bond; a group having a triple bond; and an isotopically labeled group.

17. The method of claim 1 wherein the first molecule is labeled with a first vibrational tag and the second molecule is labeled with a second vibrational tag, wherein the first vibrational tag has a first vibrational mode and the second vibrational tag has a second vibrational mode, and wherein the first selected wavelength is resonant with the first vibrational mode and the second selected wavelength is resonant with the second vibrational mode.

18. The method of claim 1 further comprising, between step c) and step d), filtering the signal beam of light resulting from the interaction of the first and second molecules in the presence of the first and second coherent lights prior to detecting the signal beam of light, wherein filtering the signal beam of light selects the wavelength of the signal beam of light in step d).

19. The method of claim 1 wherein the wavelength of the first or second coherent light is in the infrared region of the electromagnetic spectrum.

20. The method of claim 1 wherein the first or second coherent light is provided by one or more pulsed femtosecond laser beams.

21. The method of claim 1 wherein the first molecule comprises a target molecule selected from the group consisting of: a protein; a peptide; an oligonucleotide; a DNA molecule; an RNA molecule; a carbohydrate; a lipid; a pharmaceutical compound; a pharmaceutical candidate compound; a polysaccharide; and a glycoprotein, and wherein the second molecule comprises a candidate molecule selected from the group consisting of: a pharmaceutical compound; a pharmaceutical candidate compound; a protein; a peptide; an oligonucleotide; a DNA molecule; an RNA molecule; a carbohydrate; a lipid; a polysaccharide; and a glycoprotein.

22. The method of claim 1 further comprising performing steps b)-e) in the presence of a plurality of different second molecules, thereby determining the occurrence of an interaction involving the first molecule and one of the plurality of different second molecules.

23. The method of claim 22 further comprising adding multiple samples of the first molecule wherein the multiple samples of the first molecule are individually contacted with each of the plurality of different second molecules, and wherein each of the plurality of different second molecules is located in a different region of a microarray.

24. The method of claim 1, wherein the first and second coherent lights coherently excite electronic transitions in either the first molecule, the second molecule or both the first molecule and the second molecule.

25. The method of claim 24 wherein the wavelength of the first or second coherent light is in the infrared region of the electromagnetic spectrum or the visible region of the electromagnetic spectrum.

26. A method for characterizing an interaction involving a first molecule and a second molecule, the method comprising the steps of:
   a) providing the first molecule;
   b) contacting the first molecule with the second molecule;
   c) directing onto the first molecule and the second molecule a first coherent light having a first selected wavelength and a second coherent light having a second selected wavelength that is different from the first selected wavelength, wherein the first and second coherent lights have spatially separated propagation axes that intersect at the first molecule, and wherein the first and second coherent lights excite molecular vibrations in the first molecule or the second molecule or both the first and the second molecules, thereby generating a signal beam of light propagating along an axis that is spatially separated from the propagation axes of the first and second lights, the signal beam of light resulting from the interaction of the first and second molecules in the presence of the first and second coherent lights, the signal beam of light having an intensity, an amplitude, and a polarization;
   d) scanning the first coherent light over a selected first wavelength range;
   e) detecting the intensity, amplitude, or polarization of the signal beam of light;
   f) recording the intensity, amplitude, or polarization of the signal beam of light as a function of the first selected wavelength; and
   g) characterizing the interaction involving the first molecule and the second molecule by analyzing either the intensity, amplitude, or polarization of the signal beam of light as the function of the first selected wavelength.

27. The method of claim 26 wherein, in step g), characterizing the interaction involving the first molecule and the second molecule comprises measuring the time-dependent intensity of the signal beam of light, measuring the time-dependent amplitude of the signal beam of light or both the time-dependent intensity of the signal beam of light and the time-dependent amplitude of the signal beam of light.

28. The method of claim 26 further comprising the steps of:
   scanning the second coherent light over a selected second wavelength range;
   recording the intensity, amplitude, or polarization of the signal beam of light as a function of the second selected wavelength; and
   characterizing the interaction involving the first molecule and the second molecule by analyzing either the intensity, amplitude, or polarization of the signal beam of light as a function of the second selected wavelength.

29. The method of claim 28 further comprising the steps of:
   generating a first two-dimensional infrared spectrum of the first molecule;
   generating a second two-dimensional infrared spectrum when the first molecule contacts with the second molecule; and
   comparing the first and second two-dimensional infrared spectra.

30. The method of claim 26 further comprising a step selected from the group consisting of:
   determining the binding affinity of the first molecule to the second molecule;
   determining the equilibrium constant of the association of the first molecule with the second molecule;
   identifying a region of the first molecule that binds to the second molecule; and
   identifying a region of the second molecule that binds to the first molecule.

31. The method of claim 26, wherein the first and second lights coherently excite electronic transitions in either the first molecule, the second molecule or both the first molecule and the second molecule.

32. The method of claim 31 wherein the wavelength of the first or second coherent light is in the infrared region of the electromagnetic spectrum or the visible region of the electromagnetic spectrum.

* * * * *